(12) United States Patent
Ristic et al.

(10) Patent No.: US 7,388,125 B2
(45) Date of Patent: Jun. 17, 2008

(54) MAIZE CHLOROPLAST PROTEIN SYNTHESIS ELONGATION FACTORS AND METHODS OF USE FOR SAME

(75) Inventors: Zoran Ristic, Vermillion, SD (US); Shailendra K. Bhadula, Gurnee, IL (US); Genping Yang, Vermillion, SD (US); Thomas E. Elthon, Lincoln, NE (US); Jeffrey E. Habben, Urbandale, IA (US)

(73) Assignees: Pioneer Hi-Bred International, Inc., Johnston, IA (US); The University of South Dakota, Vermillion, SD (US)

( * ) Notice: Subject to any disclaimer, the term of this patent is extended or adjusted under 35 U.S.C. 154(b) by 317 days.

(21) Appl. No.: 11/005,896

(22) Filed: Dec. 7, 2004
(Under 37 CFR 1.47)

(65) Prior Publication Data

US 2005/0081265 A1    Apr. 14, 2005

Related U.S. Application Data

(63) Continuation of application No. 09/810,764, filed on Mar. 16, 2001, now abandoned.

(60) Provisional application No. 60/203,204, filed on May 11, 2000, provisional application No. 60/190,175, filed on Mar. 17, 2000.

(51) Int. Cl.
| | |
|---|---|
| C12N 15/82 | (2006.01) |
| C12N 5/10 | (2006.01) |
| C12N 15/29 | (2006.01) |
| A01H 5/00 | (2006.01) |
| A01H 5/10 | (2006.01) |

(52) U.S. Cl. .................. 800/289; 435/320.1; 435/419; 435/471; 435/468; 536/23.6; 800/287; 800/298; 800/320.1

(58) Field of Classification Search ...................... None
See application file for complete search history.

(56) References Cited

FOREIGN PATENT DOCUMENTS

EP        0 682 115 A1    11/1995

OTHER PUBLICATIONS

Bhadula, S., "Synthesis of a family of 45 ku heat shock proteins in a drought and heat resistant line of maize under controlled and field conditions", *J. Plant Phys.* 152:104-111 (1998).
Caldas, T., "Chaperone properties of bacteial elongation factor EF-Tu", *J. Biol. Chem.*, 273(19):11478-11483 (1998).
Kudlicki, W., "Renaturation of Rhodanese by translational elongation factor (EF) Tu", *J. Biol. Chem.*, 272(51):32206-32210 (1997).
Murayama et al., Plant Mol. Biol. 1993, vol. 22, pp. 767-774.
Rao et al., "Chaperone activity of recombinant maize chloroplast protein synthesis elongation factor, EF-Tu", *Eur. J. Biochem.* 271:3684-3692 (2004).
Riis, B., "Eukaryotic protein elongation factors", *TIBS* 15:420-424 (Nov. 1990).
Ristic, Z., "A maize mutant with decreased capacity to accumulate chloroplast protein synthesis elongation factor (EF-Tu) displays reduced tolerance to heat stress", Plant Science 167(1367-1374) 2004.
Ristic, Z., "Choroplast structure after water and high-temperature stress in two lines of maize that differ in endogenous levels of abscisic acid", *Int. J. Plant Sci.* 153(2):186-196 (1992).
Ristic, Z., "Dehydration avoidance and damage to the plasma and thylakoid membranes in lines of maize differing in endogenous levels of abscisic acid", *Plant Physiol.* 97:1430-1434 (1991).
Ristic, Z., "Dehydration, damage to cellular membranes, and heat-shock proteins in maize hybrids from differenct climates", *J. Plant Physiol.* 149:424-432 (1996).
Ristic, Z., "Evidence of association between specific heat-shock protein(s) and the drought and heat tolerance phenotype in maize", *J. Plant Phys.* 153:497-505 (1998).
Ristic, Z., "Heat shock proteins in two lines of Zea mays L. that differ in drought and heat resistance", *Plant Physiol.* 97:1430-1434 (1991).
Ristic, Z., "Two-dimensional gel anaylsis of 45 ku heat shock proteins from a drought and heat resistant maize line", *Plant Physiol.* (abstract) (1998).

*Primary Examiner*—Ashwin Mehta
(74) *Attorney, Agent, or Firm*—McKee, Voorhees & Sease, P.L.C.

(57) ABSTRACT

The invention discloses a novel heat shock protein with high homology to chloroplast elongation factor EF-Tu. Also disclosed is a transgenic method for enhancing tolerance to heat and drought in female reproductive organs. It involves the temporal and spatial expression of novel heat shock EF-Tu in a plant organ or plant tissue. The invention also includes expression constructs, and methods for the production of crop plants with heritable phenotypes which are useful in breeding programs designed to increase heat and drought tolerance.

20 Claims, 8 Drawing Sheets

```
AT TCCCAAATAA TCCCCACCTC CCGCTGCTGC
  TCCGCCGCCC GCCATGGCCT CCCTCACCTC GGCGTCCACT TCACTCCTCT
  TCCCGCAGGC CTCCTCATCC AGGAGCCGCA TCCGTCTCTC CACCCCCCTG
  GGCTTCTCCG CGCAGCCTGC GCGGCTGCGG AGCCAGGGG GCGGCAGTGG
  GCGCGCGGCG GCGCGGGCGC CTGCTGGTGG TGCGCGCGGC GAGGGGCAAG
  TTCGAGCGCA CCAAACCACA CGTCAACATA GGCACCATCG GCCATGTCGA
  CCACGGAAAG ACCACTCTCA CCGCCGCGCT CACCATGGTG CTCGCCTCCG
  TCGGTGGCAG CGCGCCTAAG AAGTACGACG AGATCGACGC CGCCCCCGAG
  GAGCGCGCCC GCGGTATCAC CATCAACACC GCCACCGTCG AGTACGAGAC
  CGAGACCCGC CACTACGCAC ACGTCGACTG CCCCGGCCAC GCCGACTATG
  TCAAGAATAT GATCACCGGC GCTGCGCAGA TGGACGGTGC CATCCTCGTC
  GTATCCGGTG CCGACGGGCC CATGCCGCAG ACCAAAGAGC ACATCCTCCT
  CGCCAAGCAA GTCGGTGTTC CCAAGATCGT TGTCTTCCTC AACAAGAAGG
  ACATGGTCGA CGACGAGGAG CTGCTCGAGC TCGTCGAGCT CGAGGTCCGC
  GAGCTGCTCA GCAACTACGA GTACGACGGC GACGACGTAC CAATCGTCGC
  TGGCTCCGCC CTCAAGGCGC TCGAGGCTCT CATGGTCAAC CCTGCCTTGA
  AGCGCGGCGA CGATGAGTGG GTCGACTACA TCTTCTCGTT GGTTGATAAA
  GTGGATTCCT ATATTCCAGT CCCGCAGAGG CAGACTGACC TCCCGTTCTT
  GCTCGCTGTT GAAGATGTCT TCTCCATCAC CGGTCGTGGT ACAGTTGCCA
  CTGGCCGTAT AGAGCGTGGC ACCGTCAAGA TTGGTGACAC AGTCGATATC
  GTCGGAATCC GGGACACCCG GAACTGCACG GTCACTGGTG TTGAGATGTT
  CCAGAAGACC ATGGATGATG CCATGGCCGG AGACAATGTT GGGCTGCTGC
  TCCGTGGTAT GCAGAAGGAT GACATTGAAA GAGGCATGGT GCTGGCAAAG
  CCTGGCTCTA TCACACCGCA CACCAAGTTT GAGGCTGTTG TGTATGTGCT
  TAAGAAGGAA GAGGGTGGCC GACACTCACC TTTCTTCCCT GGTTACCGCC
  CACAGTTCTA CATGCGGACA ACTGATGTG ACAGGGAGTG TGACTACGAT
  TATGAATGAC AAGGATGAGG AGGCGAAGAT GTGCATGCCT GGTGACCGTA
  TCAAAATGAT TGTTCAGCTC ATCCAGCCTG TTGCTTGTGA GCAGGGTATG
  AGGTTTGCTA TCCGTGAGGG TGGTAAGACC GTTGGTGCCG GTGTCATCAA
  CAAAATCATT GAGTAAACTG GATATAACAT ATCCACCATG AGAATTTTCC
  TTGTTTACTC AAAGCGACAT GCTCCGTAGT TGTTATTATG TGGTGAGTTT
  TAGGGGTTGC TCATGTGCAA TTGTAGTATG ACACTTTTTT TTTGTCAAGT
  GAATTTGCAT AATTTATGAC ATTCACGACA AAGATTCACA TATCTGGTTG
  CAACTCATTT GGCTAAGAGG TGCCATCTAC TGTTAAAAAA AAAAAAAAA A
```

*Fig. 7*

SEQUENCE LISTING

```
<160> NUMBER OF SEQ ID NOS: 6

<210> SEQ ID NO 1
<211> LENGTH: 20
<212> TYPE: PRT
<213> ORGANISM: Zea mays
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (16)..(16)
<223> OTHER INFORMATION: X is any amino acid

<400> SEQUENCE: 1

Ala Xaa Asn Lys Phe Glu Arg Leu Lys Pro His Val Asn Ile Gly Xaa
1               5                   10                  15

Ile Gly His Val
            20

<210> SEQ ID NO 2
<211> LENGTH: 20
<212> TYPE: PRT
<213> ORGANISM: Zea mays

<400> SEQUENCE: 2

Ala Val Lys Val Thr Ile Asn Gly Phe Gly Arg Ile Gly Thr Asn Phe
1               5                   10                  15

Leu Thr Glu Ala
            20

<210> SEQ ID NO 3
<211> LENGTH: 12
<212> TYPE: PRT
<213> ORGANISM: Zea mays
<220> FEATURE:
<221> NAME/KEY: MISC_FEATURE
<222> LOCATION: (9)..(9)
<223> OTHER INFORMATION: X is any amino acid

<400> SEQUENCE: 3

Val Val Ala Trp Tyr Asp Asn Glu Xaa Gly Tyr Ser
 1               5                   10
```

```
<210> SEQ ID NO 4
<211> LENGTH: 20
<212> TYPE: PRT
<213> ORGANISM: Zea mays
<220> FEATURE:
<221> NAME/KEY: MISC_FEATURE
<222> LOCATION: (18)..(18)
<223> OTHER INFORMATION: X is any amino acid

<400> SEQUENCE: 4

Ala Arg Gly Lys Phe Glu Arg Thr Lys Pro His Val Asn Ile Gly Thr
1               5                   10                  15

Ile Xaa His Val
            20

<210> SEQ ID NO 5
<211> LENGTH: 19
<212> TYPE: PRT
<213> ORGANISM: Zea mays
<220> FEATURE:
<221> NAME/KEY: MISC_FEATURE
<222> LOCATION: (17)..(17)
<223> OTHER INFORMATION: X can be any amino acid
<220> FEATURE:
<221> NAME/KEY: MISC_FEATURE
<222> LOCATION: (18)..(18)
<223> OTHER INFORMATION: X can be any amino acid

<400> SEQUENCE: 5

Arg Gly Lys Phe Glu Arg Thr Lys Pro Gly Val Asn Ile Gly Thr Ile
1               5                   10                  15

Xaa Xaa Val

<210> SEQ ID NO 6
<211> LENGTH: 1681
<212> TYPE: DNA
<213> ORGANISM: Zea mays

<400> SEQUENCE: 6
attcccaaat aatccccacc tcccgctgct gctccgccgc cgccatggc ctccctcacc        60 tcggcgtcca cttcactcct cttcccgcag gcctcctcat ccaggagccg catccgtctc      120
tccacccccc tgggcttctc cgcgcagcct gcgcggctgc ggagccaggg ggcggcagtg      180
ggcgcgcggc ggcgcgggcg cctgctggtg gtgcgcgcgg cgaggggcaa gttcgagcgc      240
accaaaccac acgtcaacat aggcaccatc ggccatgtcg accacggaaa gaccactctc      300
accgccgcgc tcaccatggt gctcgcctcc gtcggtggca gcgcgcctaa gaagtacgac      360
gagatcgacg ccgcccccga ggagcgcgcc cgcggtatca ccatcaacac cgccaccgtc      420
gagtacgaga ccgagacccg ccactacgca cacgtcgact gccccggcca cgccgactat      480
gtcaagaata tgatcaccgg cgctgcgcag atggacggtg ccatcctcgt cgtatccggt      540
gccgacgggc ccatgccgca gaccaaagag cacatcctcc tcgccaagca agtcggtgtt      600
cccaagatcg ttgtcttcct caacaagaag gacatggtcg acgacgagga gctgctcgag      660
ctcgtcgagc tcgaggtccg cgagctgctc agcaactacg agtacgacgg cgacgacgta      720
ccaatcgtcg ctggctccgc cctcaaggcg ctcgaggctc tcatggtcaa ccctgccttg      780
aagcgcggcg acgatgagtg ggtcgactac atcttctcgt tggttgataa agtggattcc      840
tatattccag tcccgcagag gcagactgac ctcccgttct tgctcgctgt tgaagatgtc      900
ttctccatca ccggtcgtgg tacagttgcc actggccgta tagagcgtgg caccgtcaag      960
```

```
-continued attggtgaca cagtcgatat cgtcggaatc cgggacaccc ggaactgcac ggtcactggt    1020
gttgagatgt tccagaagac catggatgat gccatggccg gagacaatgt tgggctgctg    1080
ctccgtggta tgcagaagga tgacattgaa agaggcatgg tgctggcaaa gcctggctct    1140
atcacaccgc acaccaagtt tgaggctgtt gtgtatgtgc ttaagaagga agagggtggc    1200
cgacactcac ctttcttccc tggttaccgc ccacagttct acatgcggac aactgatgtg    1260
acagggagtg tgactacgat tatgaatgac aaggatgagg aggcgaagat gtgcatgcct    1320
ggtgaccgta tcaaaatgat tgttcagctc atccagcctg ttgcttgtga gcagggtatg    1380
aggtttgcta tccgtgaggg tggtaagacc gttggtgccg gtgtcatcaa caaaatcatt    1440
gagtaaactg gatataacat atccaccatg agaattttcc ttgtttactc aaagcgacat    1500
gctccgtagt tgttattatg tggtgagttt taggggttgc tcatgtgcaa ttgtagtatg    1560
acactttttt tttgtcaagt gaatttgcat aatttatgac attcacgaca aagattcaca    1620
tatctggttg caactcattt ggctaagagg tgccatctac tgttaaaaaa aaaaaaaaaa    1680
a                                                                    1681
```

MAIZE CHLOROPLAST PROTEIN SYNTHESIS ELONGATION FACTORS AND METHODS OF USE FOR SAME

CROSS-REFERENCE TO RELATED APPLICATIONS

This application claims priority under 35 U.S.C. § 119 of U.S. Provisional Application No. 60/190,175, filed Mar. 17, 2000; U.S. Provisional Application No. 60/203,204, filed May 11, 2000; and is a continuation of U.S. application Ser. No. 09/810,764, now abandoned, filed Mar. 16, 2001, which applications are hereby incorporated by reference in their entirety.

FIELD OF THE INVENTION

This invention relates generally to the field of plant molecular biology. More specifically, this invention relates to the characterization of a novel maize chloroplast protein synthesis elongation factor (EF-Tu) protein and the use of the same for the temporal and spatial expression of genes that enhance tolerance to heat and drought conditions in plants, especially transgenic plants, to increase yield and health of plants in general as well as during periods of stress.

BACKGROUND OF THE INVENTION

Plants are often simultaneously exposed to soil drying (drought) and high-temperature stress conditions. Drought is one of the most widespread environmental variables affecting growth and development of plants. Among the prominent effects of drought stress on plant physiology and metabolism are reductions of photosynthesis, photosynthate translocation, transpiration, protein synthesis, and cell wall synthesis. Changes in gene expression also occur in response to drought stress. In addition, drought stress modifies cellular ultrastructure, including injuries to membranes.

Temperature also plays an important role in the physiological processes of plants. Increased temperatures that rise to the level of heat shock or heat stress affect cell metabolism, causing changes in the rates of biochemical reactions. Elevated temperatures further reduce photosystem II activity, photophosphorylation, photosynthetic enzyme activity, dark respiration, protein synthesis, and ion uptake. Increased temperatures also cause injuries to cellular membranes. The molecular bases of such injuries are denaturation and aggregation of proteins and formation of hexagonal II, a non-bilayer lipid phase.

The reduction in photosynthetic activity in plants associated with heat and drought stress is primarily attributable to chloroplast damage. Leaf dehydration and high temperatures can severely disrupt the ultrastructure of chloroplasts. The main damage to the chloroplast caused by water stress includes structural changes resulting from excessive swelling, distortion of the intergranal and granal lamellae, and the appearance of lipid droplets. [Poljakoff-Mayber, A (1981) Ultrastructural consequences of drought, pp. 389-403 in L. G. Paleg, ed. The physiology and biochemistry of drought resistance. Bot. Gaz. 152:186-194.] Damage to the chloroplast caused by high temperature mostly comes from detrimental effects on chloroplast envelope membranes and thylakoid membranes.

Drought and high temperatures are major limiting factors to plant productivity, often causing significant economic losses to U.S. agriculture. According to the American Association of Nurserymen, 30% of all one- and two-year-old field grown plants were lost in the Midwestern states. Cosgrove T (1988b) The industry's year in review. *American Nurseryman* 169:31-37. Numerous growers who were without irrigation lost 50% or more of their crops. Even those with on-site irrigation were unable to counter the relentless, record-breaking heat.

Indirect costs of high-temperature stresses are also noted in the costs associated with the installation and use of irrigation equipment on high value crops. Virtually all climatologists agree that high-temperature stresses will intensify due to the "greenhouse effect". Cosgrove T (1988c) Summer droughts and the "greenhouse effect". *American Nurseryman* 168:23-33. Consequently there is an increasing need in the art for new cultivars that have increased tolerance to heat stress and drought conditions to improve crop yields.

Traditional methods of improving plant heat tolerance have centered around breeding techniques. While improvements have been achieved, breeding techniques are laborious and slow. Further breeding strategies have been hampered since plant heat tolerance is a complex characteristic that is difficult to evaluate, which limits selection procedures. Thus, it would be desirable to utilize recombinant DNA technology to produce new plant varieties and cultivars in a controlled and predictable manner. To increase yield it would be especially desirable to produce crop and ornamental plants with improved tolerance to stress over a range of environmental conditions.

It can be seen from the foregoing that a need exists in the art for a transgenic method of increasing yield potential in crop and ornamental plants by improving tolerance to stresses caused by heat and drought conditions.

A rise in temperature above a certain level may result in the death of the plant. Levitt recognized the so-called heat-killing temperature as the temperature at which 50% of the plant is killed. Levitt J. (1980) Responses of Plants to Environmental Stress. Water, radiation, salt, and other stresses, 2. Academic Press, New York. However, plants exposed to sublethal high temperatures have been shown to acquire thermotolerance to otherwise lethal high temperatures. Chen H H, et al. (1982) *Crop Sci* 22:43-47. Specifically, a temperature shift of 8-10° C. above the normal growing temperature induces the synthesis of a set of new proteins, known as heat-shock proteins (HSPs). Lindquist S (1986) *Ann Rev Biochem* 55:1151-1191. The synthesis of HSPs has been observed in a variety of plant species, and the general phenotype of the heat shock response is highly conserved in all organisms. Id.

The conservative nature of HSPs and their synthesis under elevated temperatures suggest their involvement in heat resistance. Correlations between heat resistance acquired from heat pretreatments and synthesis of HSPs have been found in many species. Altschuler M., et al. (1982), Plant Mol Biol 1:103-115. In addition, recent studies have shown that specific HSPs are absolutely required for the establishment of heat resistance. Lee Y R J, et al. (1994), Plant Cell 6:1889-1897. It is generally thought that HSPs play an important role in the development of heat resistance by acting as molecular chaperones. Ellis J. (1987), Nature 328:378-379. Molecular chaperones are involved in the stabilization of proteins in a particular state of folding.

Several studies have revealed qualitative differences in the synthesis of HSPs between genotypes that differ in drought and/or heat tolerance. The heat-tolerant *Triticum aestivum* L. cv. Mustang synthesized unique HSPs that were absent in the heat-sensitive *T. aestivum* cv. Sturdy (Krishnan et al., 1989). Qualitative differences in the synthesis of HSPs have also been observed between the heat-tolerant *Gossypium barbadense* and heat-sensitive *G. hirsutum* (Fender and O'Connell, 1989). Differences in the profile of HSPs were also found between drought tolerant *Lycopersicon pennellii* and drought susceptible *L. esculentum* (Fender and O'Connell, 1990).

A recent study has revealed a genetic relationship between heat tolerance and the synthesis of specific HSPs (Park et al., 1996). A heat tolerant variant of *Agrostis palustric* Huds. synthesized heat shock polypeptides of 25 kb (HSP25) which were absent in a heat sensitive variant. Analysis of the $F_1$ progeny from these variants revealed a positive correlation between the ability to synthesize HSP25 and thermotolerance.

Few other genetic studies have been undertaken to investigate possible associations of HSPs with drought and/or heat tolerance. Further, the studies that have been conducted have not demonstrated an association between the HSPs tested and drought and/or heat tolerance. For example, when the heat-tolerant *Gossypium barbadense* was crossed to heat-sensitive *G. hirsutum*, the unique HSPs of *G. barbadense* did not associate with the heat-tolerant phenotype (Fender and O'Connell, 1989). Similarly, an interspecific cross between drought tolerant *Lycopersicon pennellii* and drought susceptible *L. esculentum* showed no association of HSPs with drought tolerance (Fender and O'Connell, 1990).

The failure of previous experiments to demonstrate association of HSPs with drought and/or heat tolerance is not surprising. Drought and heat tolerance are complex characteristics, and many factors can affect the plant's ability to tolerate stress (Levitt, 1980a, 1980b). Inability of a plant to synthesize one or few specific HSPs might be compensated by other factors that are involved in the tolerance to drought and/or heat stress.

Protein synthesis elongation factor (EF-Tu) has been intensely studied for many years in relation to its role in which peptides are elongated on ribosomes. EF-Tu is a protein of 45 kD which is involved in the elongation of polypeptides during the translational process of protein synthesis. Riis et al. (1990), Eukaryotic protein elongation factors, TIBS 15:420-424. EF-Tu is involved in the binding and transport of the appropriate codon-specified aminoacyl-tRNA to the aminoacyl site of the ribosome. EF-Tu is one of the most abundant proteins in rapidly growing *Escherichia coli* cells, with approximately 5-6 copies per ribosome. Kudlicki, W. (1997), Renaturation of Rhondanese by Translational Elongation Factor (EF) Tu, J Biol Chem 272:32206-32210.

Bacterial EF-Tu has been reported to interact with unfolded and denatured proteins in a manner similar to molecular chaperones that are involved in protein folding and protein renaturation after stress. Caldas, T. (1998), Chaperone Properties of Bacterial Elongation Factor EF-Tu, J Biol Chem 273:11478-11482. The major classes of bacterial chaperones comprise DnaK/Hsp70 (and its assistants DnaJ and GrpE), GroEL/Hsp60 (and its assistant GroES), HtpG/Hsp90, and the heat shock proteins.

The present inventors purified and isolated a novel maize EF-Tu protein and have surprisingly discovered an association between the synthesis of increased levels of EF-Tu and increased tolerance to drought and heat in maize. This chloroplast EF-Tu has been found to play a role in the development of drought and heat resistance in maize by increasing heat stability of chloroplasts. This discovery may be used in the creation of new varieties of crop plants which display increased tolerance to heat stress.

It is therefore an object of the present invention to provide a novel isolated, purified and characterized EF-Tu protein from maize. It is a further object to provide expression constructs which provide for temporal and spatial expression of EF-Tu in a transgenic plant, to increase resistance to stress through heat stability of chloroplasts.

It is yet another object of this invention to provide transgenic plant lines with heritable phenotypes which are useful in breeding programs designed to increase heat and drought tolerance in crop plants over a range of environmental conditions.

It is yet another object of this invention to produce seed which will produce plants with increased yield tolerance to heat and drought stress.

It is yet another object of this invention to provide plants, plant cells, and plant tissues containing the expression constructs of the invention.

Other objects of the invention will become apparent from the description of the invention which follows.

BRIEF SUMMARY OF THE INVENTION

The present invention comprises the isolation and characterization of a novel EF-Tu protein from maize. The invention also comprises the spatial and temporal expression of a nucleotide sequence which encodes this novel protein to increase stability of plant chloroplasts under both soil drying and heat conditions and heat conditions alone. In particular, this invention relates to the use of a novel chloroplast protein synthesis elongation factor, EF-Tu, in the creation of new varieties of crop and ornamental plants which display increased tolerance to heat and drought stress.

In this invention, new plant varieties are achieved by genetically engineering plants using a novel gene from a heat tolerant maize line, or other nucleotide sequence that encodes the EF-Tu polypeptide. In one embodiment, the invention comprises a genetic construct which upon expression in plant cells provides a DNA sequence encoding a gene product useful for increasing the production of protective EF-Tu in plant or plant tissue. In another embodiment, the invention comprises a genetic construct which provides a DNA sequence encoding a gene product useful for affecting the content of EF-Tu in a plant or plant tissue.

Synthesis of polynucleotides which encode chloroplast protein synthesis elongation factor EF-Tu stabilizes plants during stress caused by heat and drought by increasing the refolding of unfolded proteins, protecting proteins against thermal denaturation, and by forming complexes with unfolded proteins. The creation of such genetically engineered plants with increased heat tolerance will significantly reduce the costs of crop and ornamental plant production.

BRIEF DESCRIPTION OF DRAWINGS

FIG. 7 is the full length cDNA sequence of EF-Tu gene (SEQ ID NO:6).

DETAILED DESCRIPTION OF THE INVENTION

Figure 1:
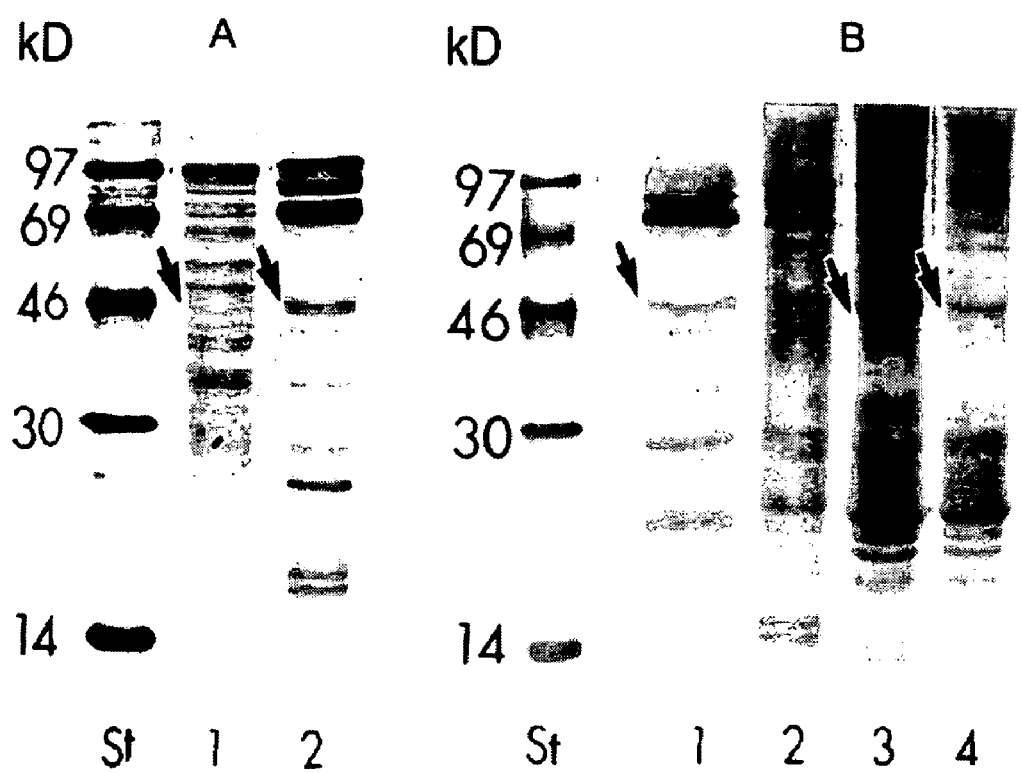
FIG. 1 is an autoradiograph showing subcellular distribution of 45 kD HSPs (EF-Tu) in the leaves of ZPBL 1304 maize line (analyzed by 1-dimensional gel electrophoresis of [$^{35}$-S]-labeled proteins). (A), Lanes 1-2, proteins isolated directly from the leaves of control (lane 1) and heat-shocked (lane 2) plants. Arrows indicate the 45 kD HSPs. (B), Lanes 1-4, pattern of HSPs in various subcellular fractions isolated from heat-stressed leaves. Lane 1, cytosolic fraction; lane 2, mitochondrial pellet; lane 3, purified chloroplasts; lane 4, chloroplast-enriched pellet. The 45 kD HSPs are shown by arrows. The 45 kD HSPs were most prevalent in the chloroplast fraction. Approximate molecular mass markers (in kilodaltons) are shown on the left side of the autoradiograph.

The present invention is based on the isolation and characterization of several isoforms of chloroplast protein synthesis elongation factor EF-Tu from a heat tolerance maize.

The proteins of the invention comprise 45 kD heat shock polypeptides which may be isolated and purified according to the teachings herein. At least three 45 kD heat shock proteins have been identified and which exhibit sequence homology to protein elongation factor EF-Tu with the following sequences: AXNKFERLKPHVNIGXIGHV (hs 2, SEQ ID NO:1), ARGKFERTKPHVNIGTIXHV (hs 4, SEQ ID NO:4) and RGKYERTKPGVNIGTIXXV (hs 5, SEQ ID NO:5). Another protein was also isolated, AVKVTINGF-GRIGTNFLTEA (SEQ ID NO:2) which bears sequence homology to Glyceraldehyde 3-phosphate dehydrogenase. This invention involves the isolation and characterization of these novel proteins as well as their substantial equivalents.

As used herein the term "EF-Tu" shall be intended to include any of the family of 45 kD heat shock proteins including SEQ ID NOS:1-3, expressed upon heat and drought stress conditions described herein and as exemplified by the maize line ZPBL 1304, and those sequences substantially equivalent thereto.

The term "substantially equivalent" as used herein means that the peptide is a substance having an amino acid sequence with at least 30%-50% homology with at least one form of the protein as disclosed herein. 80% homology is preferred and 90% homology is most preferred especially including conservative substitutions. With respect to a nucleotide sequence the term substantially equivalent means that the sequence will encode a protein or peptide that is substantially equivalent.

Homology is calculated by standard methods which involve aligning two sequences to be compared so that maximum matching occurs, and calculating the percentage of matches. Substantially equivalent substances to these include those wherein one or more of the residues of the native sequence is deleted, substituted for, or inserted by a different amino acid or acids.

Preferred substitutions are those which are conservative, i.e., wherein a residue is replaced by another of the same general type. As is well understood, naturally occurring amino acids can be sub classified as acidic, basic, neutral and polar, or neutral and nonpolar. Furthermore, three of the encoded amino acids are aromatic. It is generally preferred that peptides differing from the native MEA sequence contain substitutions which are from the same group as that of the amino acid replaced. Thus, in general, the basic amino acids Lys and Arg are interchangeable; the acidic amino acids aspartic and glutamic are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable. While proline is a nonpolar neutral amino acid, it represents difficulties because of its effects on conformation, and substitutions by or for proline are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids.

In general, whatever substitutions are made are such that the functional properties of the intact proteinaceous molecule is retained and ancillary properties, such as non-toxicity are not substantially disturbed.

A "structural gene" is a DNA sequence that is transcribed into messenger RNA (mRNA) which is then translated into a sequence of amino acids characteristic of a specific polypeptide.

An "antisense oligonucleotide" is a molecule of at least 6 contiguous nucleotides, preferably complementary to DNA (antigene) or RNA (antisense), which interferes with the process of transcription or translation of endogenous proteins so that gene products are inhibited.

A "promoter" is a DNA sequence that directs the transcription of a structural gene. Typically, a promoter is located in the 5' region of a gene, proximal to the transcriptional start site of a structural gene.

The term "expression" refers to biosynthesis of a gene product. Structural gene expression involves transcription of the structural gene into mRNA and then translation of the mRNA into one or more polypeptides.

The term "co-suppression" is a method of inhibiting gene expression in plants wherein a construct is introduced to a plant. The construct has one or more copies of sequence which is identical to or which shares nucleotide homology with a resident gene.

"Homologous recombination" is another method of inhibiting gene function by introducing a disruption construct to a plant cell under conditions which facilitate recombination of endogenous genetic material with the construct.

A "cloning vector" is a DNA molecule such as a plasmid, cosmid, or bacterial phage that has the capability of replicating autonomously in a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance or ampicillin resistance.

An "expression vector" is a DNA molecule comprising a gene that is expressed in a host cell. Typically, gene expression is placed under the control of certain regulatory elements including promoters, tissue specific regulatory elements, and enhancers. Such a gene is said to be "operably linked to" the regulatory elements.

A "recombinant host" may be any prokaryotic or eukaryotic cell that contains either a cloning vector or an expression vector. This term also includes those prokaryotic or eukaryotic cells that have been genetically engineered to contain the clone genes in the chromosome or genome of the host cell.

A "transgenic plant" is a plant having one or more plant cells that contain an expression vector. Plant tissue includes differentiated and undifferentiated tissues or plants, including but not limited to roots, stems, shoots, leaves, pollen, seeds, tumor tissue, and various forms of cells and culture such as single cells, protoplast, embryos, and callus tissue. The plant tissue may be in plant or in organ, tissue, or cell culture. These proteins can be used in techniques described herein as molecular markers in breeding to identify and/or select plants with improved heat and drought tolerance similar to maize line ZPBL 1304, as these proteins were shown to be missing in drought and heat sensitive lines.

As used herein the term "substantially tolerant" refers to the fact that the transformed and transgenic plants of this invention have tolerance to heat and/or drought conditions that adversely affects cell metabolism, plant growth, and/or development in the corresponding non-transgenic or non-transformed plant.

As used herein the term "excess heat" refers to a temperature shift of 8-10° C. above the normal growing temperature.

As used herein the term "drought" refers to a decrease in water availability to a plant.

As used herein the term "ear" shall not be limited to maize and shall include any developing female inflorescence from a plant.

As used herein the term "kernel" shall also not be limited to maize but shall include grain, or seed within a fruit.

As used herein the term "stringency" shall mean conditions of hybridization equivalent to the following: hybridized for 12 hours at 42° C. in a buffer containing 50% formamide, 5×SSPE, 26 SDS, 10× Denhardt's solution, and 100 µg/ml salmon sperm DNA, and washing with 0.1×SSC, 0.1% SDS at 55° C. and exposed to Kodak X-Omat AR film for 4 days at −70° C.

Recent studies identified the extremely drought and heat tolerance inbred line of maize, ZPBL 1304. This line was shown to be capable of withstanding severe drought and heat (45° C.) conditions without suffering severe damage. (Ristic et al. 1991). A cross made between this line, and a drought and heat sensitive line resulted in segregation of the trait in the $F_2$, indicating heritability. Moreover, the ZPBL 1304 line produced unique HSPs of 45 kD (45 HSPs) (EF-Tu) under both soil drying and heat conditions, and heat conditions alone. Similar HSPs were not produced in a drought and heat-sensitive line, ZPL 389. In addition, the 45 HSPs have not been previously found in maize, and are not common in plants.

Although differences in heat-shock protein (HSP) patterns and differences in heritable drought and/or heat tolerance have been previously documented, until now there has been no genetic evidence of an association of drought and/or heat tolerance with specific alterations in HSP expression in crop plants. According to the invention applicants have further demonstrated an association between increased levels of chloroplast protein synthesis elongation factor EF-Tu and drought and/or heat tolerance in plants. This invention further contemplates the use of EF-Tu proteins in the alteration of plants to control the expression of EF-Tu to increase plant tolerance to heat and drought conditions.

Any nucleotide sequence encoding the EF-Tu polypeptides may be used in accordance with the present invention. Methods for identifying these and other polynucleotides are known to those of skill in the art and will typically be based on screening for other plants with heat and drought tolerance which express EF-Tu during stress. Nucleotide sequences encoding this protein are easily ascertainable to those of skill in the art through Genbank or the use of plant protein codon optimization techniques known to those of skill in the art and disclosed in the references disclosed herein (for example see EPO publication number 0682115A1 and Murray et al., 1989, Nuc Acid Res., Vol. 17 No. 2, pp 447-498, "Codon Usage in Plant Genes". It is preferred to use the maize optimized coding sequences, most preferably those identified from the heat tolerant maize line ZPBL 1304. These sequences can be used not only in transgenic protocols but as tags for marker-assisted selection in plant breeding programs. The invention further contemplates the identification and use in transgenic protocols of the regulatory elements associated with these sequences. For example an EF-Tu promoter could be used for spatial and temporal control of other structural genes to induce expression during periods of stress. Methods of identifying gene regulatory regions are known to those of skill in the art and are disclosed in the references incorporated herein.

The role of these EF-Tu proteins can be exploited to engineer plants with improved stress tolerance. For example, transgenic expression of the nucleotide that encodes EF-Tu can be accomplished at an appropriate time to increase the levels of the protein in selected tissues at critical times such as during periods of high temperatures and/or drought, thereby increasing the stress tolerance of the plant. According to the invention, transgenic expression of a nucleotide encoding EF-Tu is used to engineer plants with improved drought and stress tolerance. Expression of EF-Tu may also be timed and spatially directed through the use of regulatory elements to increase tolerance at critical periods.

Thus, the invention contemplates in one embodiment the expression of 45 kD heat shock EF-Tu encoding nucleotide sequences during vulnerable periods primarily those involved with stress, where yield is most significantly affected by heat and drought stress during any time in plant development.

As used herein the term "stress" shall include any period in plant development where yield may be more significantly impacted by stress such as heat, drought, over-crowding, etc. This can include the exponential growth phase of the ear during which biomass is accumulated and the lag phase of kernel development as more fully described herein and in the following references. Set and Flower Synchrony within the Ear of Maize II. Plant Population Effects", Crop Science, 37: 448-455 (March-April 1997); and Shaw, Robert "Climate Requirement", Corn Improvement, $3^{rd}$ ed., Chapter 10, pp. 609-638).

The examples and discussion herein may specifically reference maize, however the teachings herein are equally applicable to any other grain or flowering crop.

According to the invention, a genetic construct is disclosed which causes expression of heat shock EF-Tu nucleotide sequence at a time and location to maximize plant tolerance to heat and drought conditions, typically during very vulnerable periods primarily such as stress. The spatial and temporal expression of EF-Tu can be achieved using different types of promoters. Promoters useful for the invention are promoters which would cause the temporal and spatial expression of a gene product during periods of stress, primarily during stress as defined herein and can be constitutive, inducible, or tissue specific.

For example, seed specific promoters can be used to cause EF-Tu expression during seed development, pre-pollination promoters can also be used or stress inducible promoters can be used to cause EF-Tu expression during periods of stress. The optimization of promoters to achieve the objectives of the invention is considered routine and easily ascertainable by those of skill in the art and is intended to be within the scope of the invention.

In another preferred embodiment leaf specific promoters can be used. Examples include as the AS-1 promoter disclosed in U.S. Pat. No. 5,256,558 to Coruzzi and the RBCS-3A promoter isolated from pea the RBCS-3A gene disclosed in U.S. Pat. No. 5,023,179 to Lam et al.

At its simplest, one embodiment of the invention comprises a nucleotide construct comprising an EF-Tu-encoding nucleotide sequence, a regulatory promoter to regulate temporal tissue and spatial expression during periods of stress, and termination sequences operably linked to said nucleotide sequence.

Identification of other polynucleotides which may be useful in the invention will typically be based on screening procaryotic or eukaryotic organisms which produce isoforms of EF-Tu under heat shock conditions. EF-Tu is highly conserved among different species, and a large number of EF-Tu prokaryotic and eukaryotic sequences have already been determined by cDNA cloning.

The polynucleotides useful in the invention can be formed from a variety of different polynucleotides (e.g., genomic or cDNA, RNA, synthetic oligonucleotides, and polynucleotides), as well as by a variety of different techniques. As used herein, a polynucleotide is a sequence of either eukaryotic or prokaryotic synthetic invention.

In a preferred embodiment, the invention comprises the use of the nucleotide sequence which encodes hs proteins, 2, 3, or 4 from inbred maize line ZPBL 1304 encoding EF-Tu. This can allow for hybrid plant or seed production, once transgenic inbred parental lines have been established.

The invention is not limited to any plant type and can be used for any crop or ornamental plant species for which it is desirable to increase yield. The methods of the invention may be applicable to any species of plant to enhance heat and drought tolerance by affecting the stability of chloroplasts.

The nucleotide constructs of the present invention will share similar elements, which are well known in the art of plant molecular biology. For example, in each construct the DNA sequences of interest will preferably be operably linked (i.e., positioned to ensure the functioning of) to a promoter which allows the DNA to be transcribed (into an RNA transcript) and will comprise a vector which includes a replication system. In preferred embodiments, the DNA sequence of interest will be of exogenous origin in an effort to prevent co-suppression of the endogenous genes.

Promoters (and other regulatory elements) may be heterologous (i.e., not naturally operably linked to a DNA sequence from the same organism). Promoters useful for expression in plants are known in the art and can be inducible, constitutive, tissue-specific, derived from eukaryotes, prokaryotes or viruses, or have various combinations of these characteristics.

In choosing a promoter to use in the methods of the invention, it may be desirable to use a tissue-specific or developmentally regulated promoter. A tissue-specific or developmentally regulated promoter is a DNA sequence which regulates the expression of a DNA sequence selectively in the cells/tissues of a plant critical to seed set and/or function and/or limits the expression of such a DNA sequence to the period of seed maturation in the plant. Any identifiable promoter may be used in the methods of the present invention which causes expression during stress as defined herein. It may also be advantageous to use a stress inducible promoter to provide expression of the construct during periods of stress.

Differential screening techniques can be used to isolate promoters expressed in developing female reproductive organs prior to, and immediately after, flowering (0-10 DAP). Promoters identified in this manner include NUC1 which is expressed in the nucleus prior to fertilization (Doan, D. N. P., et al. (1996) Plant Mol. Biol. 31:877-886, which is incorporated herein by reference).

Promoters which are preferred for the invention and would be acceptably timed to stress follow. These and other such promoters are known and accessible through sources such as Genbank: barley promoter B22E: 69 NAL Call No. 442.8 Z34 "Primary Structure of a Novel Barley Gene Differentially Expressed in Immature Alleurone Layers," Klemsdae, S. S. et al., Springer Int'l 1991 Aug., Molecular and General Genetics, Vol. 228(½) p. 9-16, 1991. Expression of B22E is specific to the pedicel in developing maize kernels, Zag2: 134 NAL Call. No.: QK725. P532 Identification and molecular characterization of ZAG1, the maize homolog of the Arabidopsis floral homeotic gene AGAMOUS. Schmidt, R. J.; Veit, B.; Mandel, M. A.; Mena, M.; Hake, S.; Yanofsky, M. F. Rockville, Md.: American Society of Plant Physiologists, c1989-; 1993 July The Plant Cell v. 5(7): p 729-737; 1993 July includes references. Zag2 transcripts can be detected 5 days prior to pollination to 7 to 8 DAP, and directs expression in the carpel of developing female inflorescences and Cim1 which is specific to the nucleus of developing maize kernels. Cim1 transcript is detected 4 to 5 days before pollination to 6 to 8 DAP. Other useful promoters include any promoter which can be derived from a gene whose expression is maternally associated with developing female florets.

Table 1 shows a list of preferred promoters including their timing of expression (DAP=days after pollination).

TABLE 1

Promoter Expression Summary

| Promoter | Source | Primary Tissue | Temporal |
|---|---|---|---|
| ltp2 | barley cDNA | aleurone | <6-24+ DAP |
| cim1 | maize EST | pericarp (under silk scar) | 0-12+ DAP |
| nuc1-c | barley cDNA | nucellus, pedicel forming region | 1-12+ DAP |
| mze40-2 [maize B22e] | maize EST | gloom, pericarp, pedicel forming region, low in scutellum | <4-28+ DAP |
| b22e | barley genomic | aleurone, embryo scutellum, pedicel forming region | <5-30+ DAP |
| zag2 | maize, EST | floret, ovule | <0-22 DAP |
| end1 | maize, cDNA | endosperm transfer cells | 6-14 DAP |
| betl1 | maize, cDNA | endosperm transfer cells | 8-30+ DAP |

For example, a construct useful for the present invention might include a maize gene encoding EF-Tu operably linked to the B22e promoter for increased heat and drought stability 5 to 28 days after pollination.

Other promoters which are seed or embryo specific and may be useful in the invention include patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259:149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include Arabidopsis thaliana 2S seed storage protein gene promoter to express enkephalin peptides in Arabidopsis and Brassica napus seeds (Vanderkerckhove et al., Bio/Technology 7:L929-932 (1989)), been lectin and bean β-phaseolin promoters to express luciferase (Riggs et al., Plant Sci. 63:47-57 (1989)), and wheat glutenin promoters to express chloramphenicol acetyl transferase (Colot et al., EMBO J 6:3559-3564 (1987)).

Any inducible promoter can be used in the instant invention. See Ward et al. Plant Mol. Biol. 22: 361-366 (1993). Exemplary inducible promoters include, but are not limited to, that from the ACE1 system which responds to copper (Mett et al. PNAS 90: 4567-4571 (1993)); In2 gene from maize which responds to benzenesulfonamide herbicide safeners (Hershey et al., Mol. Gen. Genetics 227: 229-237 (1991) and Gatz et al., Mol. Gen. Genetics 243: 32-38 (1994)) or Tet repressor from Tn10 (Gatz et al., Mol. Gen. Genet. 227: 229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88: 0421 (1991).

Many different constitutive promoters can be utilized in the instant invention. Exemplary constitutive promoters include, but are not limited to, the promoters from plant viruses such as the 35S promoter from CaMV (Odell et al., Nature 313: 810-812 (1985) and the promoters from such genes as rice actin (McElroy et al., Plant Cell 2: 163-171 (1990)); ubiquitin (Christensen et al., Plant Mol. Biol 12: 619-632 (1989) and Christensen et al., Plant Mol. Biol. 18: 675-689 (1992)): pEMU (Last et al., Theor. Appl. Genet. 81: 581-588 (1991)); MAS (Velten et al., EMBO J. 3: 2723-2730 (1984)) and maize H3 histone (Lepetit et al., Mol. Gen. Genet. 231: 276-285 (1992) and Atanassova et al., Plant Journal 2 (3): 291-300 (1992)).

The ALS promoter, a Xbal/Ncol fragment 51 to the Brassica napus ALS3 structural gene (or a nucleotide sequence that has substantial sequence similarity to said Xbal/Ncol fragment), represents a particularly useful constitutive promoter. See PCT application WO96/30530.

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art. See, for example, Sullivan, T., "Analysis of Maize Brittle-1 Alleles and a Defective Suppressor-Mutator-Induced Mutable Allele", The Plant Cell, 3:1337-1348 (1991), Becker et al., Plant Mol. Biol.20: 49 (1992), Close, P. S., Master's Thesis, Iowa State University (1993), Knox, C., et al., "Structure and Organization of Two Divergent Alpha-Amylase Genes From Barley", Plant Mol. Biol. 9: 3-17 (1987), Lerner et al., Plant Physiol.91: 124-129 (1989), Fontes et al., Plant Cell 3:

483-496 (1991), Matsuoka et al., *Proc. Natl. Acad. Sci.* 88: 834 (1991), Gould et al., *J. Cell Biol* 108: 1657 (1989), Creissen et al., *Plant J.* 2: 129 (1991), Kalderon, D., Robers, B., Richardson, W., and Smith A., "A short amino acid sequence able to specify nuclear location", *Cell* 39: 499-509 (1984), Stiefel, V., Ruiz-Avila, L., Raz R., Valles M., Gomez J., Pages M., Martinez-Izquierdo J., Ludevid M., Landale J., Nelson T., and Puigdomenech P., "Expression of a maize cell wall hydroxyproline-rich glycoprotein gene in early leaf and root vascular differentiation", *Plant Cell* 2: 785-793 (1990).

Selection of an appropriate vector is relatively simple, as the constraints are minimal. The minimal traits of the vector are that the desired nucleic acid sequence be introduced in a relatively intact state. Thus, any vector which will produce a plant carrying the introduced DNA sequence should be sufficient. Typically, an expression vector contains (1) prokaryotic DNA elements encoding for a bacterial replication origin and an antibiotic resistance marker to provide for the growth and selection of the expression vector in a bacterial host; (2) DNA elements that control initiation of transcription, such as a promoter; (3) DNA elements that control the processing of transcripts such as transcription termination/polyadenylation sequences; and (4) a reporter gene. Useful reporter genes include β-glucuronidase, β-galactosidase, chloramphenicol acetyltransferase, luciferase, kanamycin or the herbicide resistance genes PAT and BAR. Preferably, the reporter gene is kanamycin or the herbicide resistance genes PAT and BAR. The BAR or PAT gene is used with the selecting agent Bialaphos, and is used as a preferred selection marker gene for plant transformation (Spencer, et al. (1990) J. Thero. Appl'd Genetics 79:625-631).

One commonly used selectable marker gene for plant transformation is the neomycin phosphotransferase II (nptll) gene, isolated from transposon Tn5, which when placed under the control of plant regulatory signals confers resistance to kanamycin. Fraley et al., *Proc. Natl. Acad. Sci. U.S.A.*, 80: 4803 (1983). Another commonly used selectable marker gene is the hygromycin phosphotransferase gene which confers resistance to the antibiotic hygromycin. Vanden Elzen et al., Plant Mol. Biol., 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86: 1216 (1988), Jones et al., Mol. Gen. Genet., 210: 86 (1987), Svab et al., Plant Mol. Biol. 14: 197 (1990), Hille et al., Plant Mol. Biol. 7: 171 (1986). Other selectable marker genes confer resistance to herbicides such as glyphosate, glufosinate or broxynil. Comai et al., Nature 317: 741-744 (1985), Gordon-Kamm et al., Plant Cell 2: 603-618 (1990) and Stalker et al., Science 242: 419-423 (1988).

Other selectable marker genes for plant transformation are not of bacterial origin. These genes include, for example, mouse dihydrofolate reductase, plant 5-enolpyruvylshikimate-3 -phosphate synthase and plant acetolactate synthase. Eichholtz et al., Somatic Cell Mol. Genet. 13: 67 (1987), Shah et al., Science 233: 478 (1986), Charest et al., Plant Cell Rep. 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., Plant Mol. Biol. Rep. 5: 387 (1987)., Teeri et al., EMBO J. 8: 343 (1989), Koncz et al., Proc. Natl. Acad. Sci. U.S.A. 84:131 (1987), De Block et al., EMBO J. 3: 1681 (1984). Another approach to the identification of relatively rare transformation events has been use of a gene that encodes a dominant constitutive regulator of the *Zea mays* anthocyanin pigmentation pathway. Ludwig et al., Science 247: 449 (1990).

Recently, in vivo methods for visualizing GUS activity that do not require destruction of plant tissue have been made available. Molecular Probes Publication 2908, Imagene Green, p. 1-4 (1993) and Naleway et al., *J. Cell Biol.*115: 151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Genes included in expression vectors must be driven by a nucleotide sequence comprising a regulatory element, for example, a promoter. Several types of promoters are now well known in the transformation arts, as are other regulatory elements that can be used alone or in combination with promoters.

A general description of plant expression vectors and reporter genes can be found in Gruber, et al. (Gruber et al. (1993) Vectors for Plant Transformation. In: Methods in Plant Molecular Biology and Biotechnology. Glich et al., eds. (CRC Press), pp. 89-119.

Expression vectors containing genomic or synthetic fragments can be introduced into protoplast or into intact tissues or isolated cells. Preferably, expression vectors are introduced into intact tissue. General methods of culturing plant tissues are provided for example by Maki, et al. (Maki, et al. (1993) Procedures for Introducing Foreign DNA into Plants: In: Methods in Plant Molecular Biology & Biotechnology; Glich et al. eds. (CRC Press), pp. 67-88; Philips, et al. (1988) Cell-Tissue Culture and In Vitro Manipulation. In Corn & Corn Improvement, 3$^{rd}$ ed. Sprague, et al. eds. (American Society of Agronomy Inc.), pp. 345-387).

Methods of introducing expression vectors into plant tissue include the direct transfection or co-cultivation of plant cell with *Agrobacterium tumefaciens* (Horsch et al. (1985) Science, 227:1229). Descriptions of *Agrobacterium* vector systems and methods for *Agrobacterium*-mediated gene transfer are provided by Gruber et al. (supra).

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

*Agrobacterium*-Mediated Transformation

One method for introducing an expression vector into plants is based on the natural transformation system of *Agrobacterium*. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant. Sci.10: 1 (1991). Descriptions of *Agrobacterium* vector systems and methods for *Agrobacterium*-mediated gene transfer are provided by Gruber et al., supra, Miki et al., supra, and Moloney et al., Plant Cell Reports 8: 238 (1989). See also, U.S. Pat. No. 5,591,616, issued Jan. 7, 1997.

Direct Gene Transfer

Despite the fact the host range for *Agrobacterium*-mediated transformation is broad, some major cereal crop species and gymnosperms have generally been recalcitrant to this mode of gene transfer, even though some success has recently been achieved in rice and maize. Hiei et al., The Plant Journal 6: 271-282 (1994); U.S. Pat. No. 5,591,616, issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 mm. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5: 27 (1987), Sanford, J. C., Trends Biotech. 6: 299 (1988), Klein et al., Bio/Technology 6: 559-563 (1988), Sanford, J. C., Physiol Plant 79: 206 (1990), Klein et al., Biotechnology 10: 268 (1992). In maize, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., Bio/Technology 9: 996 (1991). Alternatively, liposome or spheroplast fusion have been used to introduce expression vectors into plants. Deshayes et al., EMBO J., 4: 2731 (1985), Christou et al., Proc Natl. Acad. Sci. U.S.A. 84: 3962 (1987). Direct uptake of DNA into protoplasts using CaCl2 precipitation, polyvinyl alcohol or poly-L-ornithine have also been reported. Hain et al., Mol. Gen. Genet.199: 161 (1985) and Draper et al., Plant Cell Physiol.23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., Plant Cell 4: 1495-1505 (1992) and Spencer et al., Plant Mol. Biol. 24: 51-61 (1994).

Following transformation of maize target tissues, expression of the above-described selectable marker genes allows for preferential selection of transformed cells, tissues and/or plants, using regeneration and selection methods now well known in the art.

After transformation of a plant cell or plant, plant cells or plants transformed with the desired DNA sequences integrated into the genome can be selected by appropriate phenotypic markers. Phenotypic markers are known in the art and may be used in this invention.

Confirmation of transgenic plants will typically be based on an assay or assays or by simply measuring stress response. Transformed plants can be screened by biochemical, molecular biological, and other assays. Various assays may be used to determine whether a particular plant, plant part, or a transformed cell shows an increase in enzyme activity or carbohydrate content. Typically, the change in expression or activity of a transformed plant will be compared to levels found in wild type (e.g., untransformed) plants of the same type. Preferably, the effect of the introduced construct on the level of expression or activity of the endogenous gene will be established from a comparison of sibling plants with and without the construct. EF-Tu levels can be measured, for example, by Northern blotting, primer extension, quantitative or semi-quantitative PCR (polymerase chain reaction), and other methods well known in the art (See, e.g., Sambrook, et al. (1989). Molecular Cloning, A Laboratory Manual, second edition (Cold Spring Harbor Laboratory Press), Vols. 1-3). Protein can be measured in a number of ways including immunological methods (e.g., by Elisa or Western blotting). EF-Tu activity can be measured in various assays as described in Smith (Smith, A. M. (1990). In: Methods in Plant Biochemistry, Vol. 3, (Academic Press, New York), pp. 93-102).

Normally, regeneration will be involved in obtaining a whole plant from a transformation process. The term "regeneration" as used herein, means growing a whole plant from a plant cell, a group of plant cells, a plant part, or a plant piece (e.g., from a protoplast, callus, or a tissue part).

The foregoing methods for transformation would typically be used for producing transgenic inbred lines. Transgenic inbred lines could then be crossed, with another (non-transformed or transformed) inbred line, in order to produce a transgenic hybrid maize plant. Alternatively, a genetic trait which has been engineered into a particular maize line using the foregoing transformation techniques could be moved into another line using traditional backcrossing techniques that are well known in the plant breeding arts. For example, a backcrossing approach could be used to move an engineered trait from a public, non-elite line into an elite line, or from a hybrid maize plant containing a foreign gene in its genome into a line or lines which do not contain that gene. As used herein, "crossing" can refer to a simple X by Y cross, or the process of backcrossing, depending on the context.

Various plants will be suitable targets for enhancing sink strength in female reproductive organs with the acid invertase and AGPase genes. In particular, the methods of the invention described herein may be applicable to any crop species including but not limited to barley, sorghum, wheat, maize, soybean, and rice.

Parts obtained from the regenerated plant, such as flowers, pods, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences.

EF-Tu levels and the activity of EF-Tu are preferably determined as set forth in the examples.

Once a transgenic plant is produced having a desired characteristic, it will be useful to propagate the plant and, in some cases, to cross to inbred lines to produce useful hybrids.

In seed propagated crops, mature transgenic plants may be self crossed to produce a homozygous inbred plant. The inbred plant produces seed containing the genes for the newly introduce trait. These seeds can be grown to produce plants that will produce the selected phenotype.

The following examples are offered to illustrate but not limit the invention. Thus, they are presented with the understanding that various formulation modifications as well as method of delivery modifications may be made and still be within the spirit of the invention.

EXAMPLE 1

Chloroplast Structure After Water and High-Temperature Stress in Heat-Resistant and Non-Heat-Resistant Strains of Maize Materials and Methods Maize line ZPBL 1304 and maize line ZPL 389 were analyzed. In order to compare lines at similar developmental stages, lines that have the same time to flowering were selected.

Experimental Setup and Growth Conditions

Experimental setup and growth conditions were similar to those described by Ristic et al. (1991). In two experiments, experiment A had six replicates, and experiment B had five replicates. Experimental setup and growth conditions were identical for both experiments unless otherwise stated. For each replicate, 11 kernels of each line were sown in each of two pots (pot diameters at the top and the bottom were 20.5 cm and 14 cm, respectively; pot height, 20 cm) containing a mixture of soil: peat: sand (3:1:1, v/v/v). Plants were grown under controlled environmental conditions—12-h photoperiod, 280 µmol m$^{-2}$ sec$^{-1}$ PPFD, 24 C/18 C day/night temperature, and 70% relative humidity day and night—and were watered daily up to the second leaf stage, for 13 d. Subsequently the plants were divided into control and experimental groups, one pot per group. The control group was watered daily until the end of the experiment. The experimental group was not watered for 7 d followed by exposure to high temperature (45 C) for 6 h and 24 h, in experiments A and B, respectively. Treated plants were then rewatered and allowed to recover for 6 d. Leaf samples for relative water content (RWC) and transmission electron microscopy (TEM) were obtained from the second leaf blades from one randomly selected plant from each group. Data from the control and the experimental group were collected at the same time. The third leaf blades were expanded in plants of both lines at the time when samples for RWC and TEM were collected.

Relative Water Content and Transmission Electron Microscopy

Relative water content was determined after exposure to high temperature and on the third and the sixth day of recovery. Relative water content was determined according to Henson et al. (1980). Relative water content was calculated as RWC=(fresh weight−dry weight)/(turgid weight−dry weight)×100. Turgid weight was determined after imbibition of leaf blades in distilled water in sealed glass tubes for 4 h at room temperature followed by overnight storage at 5° C., and dry weight was determined after 48 h at 80° C.

Leaf samples for TEM (about 1 mm$^2$) were fixed in 4% glutaraldehyde and 4% paraformaldehyde, in 0.1 M phosphate buffer (pH 7), for 2 h at 4° C. Postfixation with 2% osmium tetroxide in the above buffer was for 2 h at room temperature. Specimens were dehydrated in a graded series of acetone (30%, 50%, 70%, 80%, 90%, 100%) and left, first in a mixture of Spurr embedding medium (Spurr 1969) and 100% acetone (1:1, v/v) for 2 h at room temperature and then in pure epoxy resin overnight at 4 C. The embedding was completed in 24 h at 60° C. Thin sections (60-99 nm) were cut on a Reichert Ultracut E ultramicrotome, using a diamond knife. Sections were double-stained, first with 4% uranyl acetate in 70% ethanol for 45-60 min and then with 0.2% aqueous lead citrate (Venable and Coggeshall 1965) for 2-3 min. Specimens were viewed with a Philips 201 TEM at 60 kV, equipped with a 35-mm camera. For each plant an average of 120-150 randomly chosen mesophyll cells were examined.

Results

Chloroplast Structure After Exposure to 7-day Soil Drying Followed by 6-h High-Temperature (45 C) Stress The stress tolerant ABA line ZPBL 1304.—Chloroplasts from the control plants were well developed, with distinctive envelopes and grana. Exposure to stress conditions did not affect their structure. Chloroplast-envelope membranes and grana were well defined. In addition, the frequency of plastoglobuli appeared to be similar between chloroplasts from the control and the treated plants. Chloroplast structure in recovered plants did not differ from that in controls.

The stress sensitive ABA line ZPL 389.—Chloroplast structure in well-watered plants was similar to that in the control group of ZPBL 1304. Stress conditions affected chloroplast structure to a great extent, although some of the chloroplasts appeared normal. In affected chloroplasts, envelope membranes were broken and not distinctive. In many grana, swelling of thylakoids occurred; consequently, the intrathylakoid space was increased and numerous vesicles were formed.

Three days after rewatering, most of the chloroplasts appeared normal. However, some were not fully recovered even though their envelope membranes were distinct; in these chloroplasts, chloroplast internal organization was not repaired completely, and many vesicles were still present. After a 6-day recovery period, all of the chloroplasts had recovered, and their structure was similar to that in the control plants.

Chloroplast Structure After Exposure to 7-Day Soil Drying Followed by 24-h High-Temperature (45 C) Stress ZPBL 1304. —In control plants the chloroplasts had normal structure. In plants exposed to stress, four groups of chloroplasts were observed. In the first group, chloroplast structure was similar to that in the control plants. In the second group, chloroplasts were also similar to those in unstressed plants, but their shape was irregular. In chloroplasts from the third group, envelope membranes were broken and not distinct, but granule structure appeared unaffected. Chloroplasts from the fourth group had distinct chloroplast envelopes, even though they were occasionally broken. Their internal organization, however, was affected by stress conditions to a high degree. There were swollen thylakoid membranes and numerous internal vesicles.

Three days after rewatering, the majority of chloroplasts had recovered. Chloroplast envelopes and grana were distinct. Some of the chloroplasts, however, seemed to be still in the process of recovery. A structure that has a distinct envelope and many internal vesicles was interpreted as a chloroplast that underwent structural modification during the stress treatment; the internal vesicles likely represent swollen thylakoids. During the recovery process, these vesicles reassemble and form grana. In the final stage almost all the thylakoids reassembled, forming grana, even though some of them were swollen. The chloroplast envelope in some chloroplasts, however, was incomplete; occasionally it was broken and swollen.

The structural organization of chloroplasts appeared normal after a 6-day recovery period. Only a few chloroplasts remained in the process of recovery. In these chloroplasts, distinct chloroplast-envelope membranes, many grana, and starch grains were observed, but internal vesicles were still present.

ZPL 389.—Chloroplasts from the control plants were normal in their structure. After exposure to 7-day soil drying followed by 45 C, chloroplast structure was severely disrupted. Chloroplast-envelope membranes were not visible, and grana were barely recognizable. The shape of the chloroplasts was also irregular, and huge, darkly stained plastoglobuli were visible in many of them.

Chloroplasts from ZPL 389 were not restored after the 3-day recovery period. On the contrary, their structure was even more disrupted than in chloroplasts observed immediately after the stress. They were darkly stained and had many lipid droplets and poorly organized membranes. Six days after recovery, chloroplast structure was barely different from that after the 3-day recovery. Although some chloroplasts had granal structure again, none had intact envelope membranes.

Discussion

Water shortage and high-temperature stress caused alterations in the structure of chloroplasts from leaf mesophyll cells in the stress tolerant line of maize ZPBL 1304 and the stress sensitive line ZPL 389. Comparable results under water stress have been reported in chloroplast structure from the *Zea mays* cultivar Wisconsin 575 (Giles et al. 1974), *Sorghum bicolor* Moench (Giles et al. 1976), *Gossypium hirsutum* L. (Vieira da Silva et al. 1974; Ackerson and Hebert 1981), *Cicer arientinum* (Alieva et al. 1971), and *Talbotia elegans* Balf. (Hallam and Luf 1980). Similar modifications in chloroplast structure under soil drying and high-temperature stress conditions have been found in two maize lines (Polj 17 and F-2) that differ in endogenous levels of ABA and drought resistance (Ristic and Cass 1991a).

It is likely that chloroplast damage in ZPBL 1304 and ZPL 389 was partly a result of leaf dehydration (Ristic and Cass, unpub. data). Dehydration in ZPBL 1304 was negligible (RWC=97%±2% SE) after heating for 6 h, and 52% after heating for 24 h. Leaves of ZPL 389 suffered dehydration of 44% after exposure to 6-h high-temperature stress, and 89% after exposure to 24-h high-temperature stress. Leaf dehydration was reversible in 6-h heated plants of ZPL 389 and 24-h heated plants of ZPBL 1304, and irreversible in 24-h heated plants of ZPL 389. A similar pattern of leaf dehydration in these two lines under stress conditions was indicated by changes in leaf turgor and water potential; leaves of 13-day water-stressed plants of lines ZPBL 1304 and ZPL 389 had turgor pressures of −0.01 MPa and −0.17 MPa, and water potentials of −1.18 MPa and −1.37 MPa, respectively (Pekic and Quarrie 1987).

In addition to dehydration, high temperature per se seems to be operative in damaging the chloroplasts, since high temperatures are known to have detrimental effects on chloroplast membranes (Krause and Santarius 1975; Bauer and Senser 1979; Armond et al. 1980; McCain et al. 1989). Heat-induced damage to chloroplasts has been reported in intact plants of *Hedera helix* L. (Bauer and Senser 1979), leaves of *Acer platanoides* L. (McCain et al. 1989), and isolated chloroplasts of *Spinacia oleracea* L. (Krause and Santarius 1975) and *Vicia faba* L. (Gounaris et al. 1983).

Although stress affected both lines of maize, there were clear differences in chloroplast structure under stress conditions between ZPBL 1304 and ZPL 389. Chloroplasts in ZPBL 1304 were less affected by stress conditions than those in ZPL 389, and this was apparent after both stress treatments. It can be argued that these differences do not reflect differences in the stability of chloroplast membranes between the two genotypes, since the two lines were not dehydrated to a similar extent. However, when dehydration in ZPBL 1304 (RWC=48%÷4% SE) reached a level similar to that in ZPL 389 (RWC=56%±8% SE) (Ristic and Cass, unpub. data) chloroplasts in ZPBL 1304 were affected less than those from ZPL 389. Comparison of chloroplasts in ZPL 389 after 7-day soil drying followed by 6-h heat stress and chloroplasts in ZPBL 1304 after 7-day soil drying followed by 24-h heat stress illustrated this point.

The results on chloroplast structure agree with the results on leaf physiological characteristics in ZPBL 1304 and ZPL 389 after exposure to soil drying and high-temperature (45° C.) stress conditions (see Introduction). Furthermore, the results on chloroplast structure also agree with the results on the pattern of synthesis of heat-shock proteins (HSPs) in ZPBL 1304 and ZPL 389 (Ristic et al. 1991). A unique band of HSPs at approximately 45 kD was found in the heated (45° C.) plants of ZPBL 1304 that was not observed in the heated (45° C.) plants of ZPL 389. Although the function of HSPs is not clear, it is possible that the pattern of HSP synthesis in lines ZPBL 1304 and ZPL 389 had an impact on the stability of chloroplast membranes in these two lines since in maize a subset of HSPs has been shown to be internalized by the chloroplasts (Vierling et al. 1986).

It has been reported that ABA has destructive effects on ultrastructural features of chloroplasts in *Triticum aestivum* L., *Avena sativa* L. (Wellburn and Wellburn 1973), and *Pisum sativum* L. (Krendeleva et al. 1988). This might indicate that increased ABA levels could have negative effects on chloroplast structure. The results of this study did not show this. It is possible that if there were any effects of ABA on chloroplast structure in line ZPBL 1304 (high-ABA line), they would have been much less than the negative effects of stress conditions on chloroplast structure in line ZPL 389 (low-ABA line).

It is hypothesized that the differences in the structure of stress-damaged chloroplasts between ZPBL 1304 and ZPL 389 were partly the result of genotypic differences in the thermal sensitivity of chloroplast membranes. Photosynthetic membranes of vascular plants contain a high proportion of polyunsaturated lipids, and the thermal stability of chloroplast membranes depends to a great extent on the level of poly-unsaturated lipids. Thomas et al. (1986) suggested that decreased lipid unsaturation increases the temperature at which changes in the structure of chloroplast membranes occur. Even though the lipid composition of photosynthetic membranes in these maize lines is not known, it is possible that the differences in chloroplast structure between lines ZPBL 1304 and ZPL 389 under stress conditions were partly the result of differences in the lipid composition of their membranes.

EXAMPLE 2

Measurement of Steady State Levels of EF-Tu mRNA in the Drought and Heat Tolerant ZPBL 1304 Maize Line Under Normal and Heat Stress Conditions Materials and Methods The steady state levels of ZPBL 1304 EF-Tu mRNA were measured using Northern blot analysis. Total leaf RNA was isolated from control and heat-stressed plants of ZPBL 1304, using a commercial RNA isolation kit (Ambion). The RNA was fractionated using 1% agarose gel electrophoresis and transferred onto positively charged nylon membrane. Cross linking was achieved by baking the membrane at 80° C. for 2 h. A maize EF-Tu EST was used as a DNA probe for hybridization of the RNA blots.

Results and Conclusions

Figure 4:
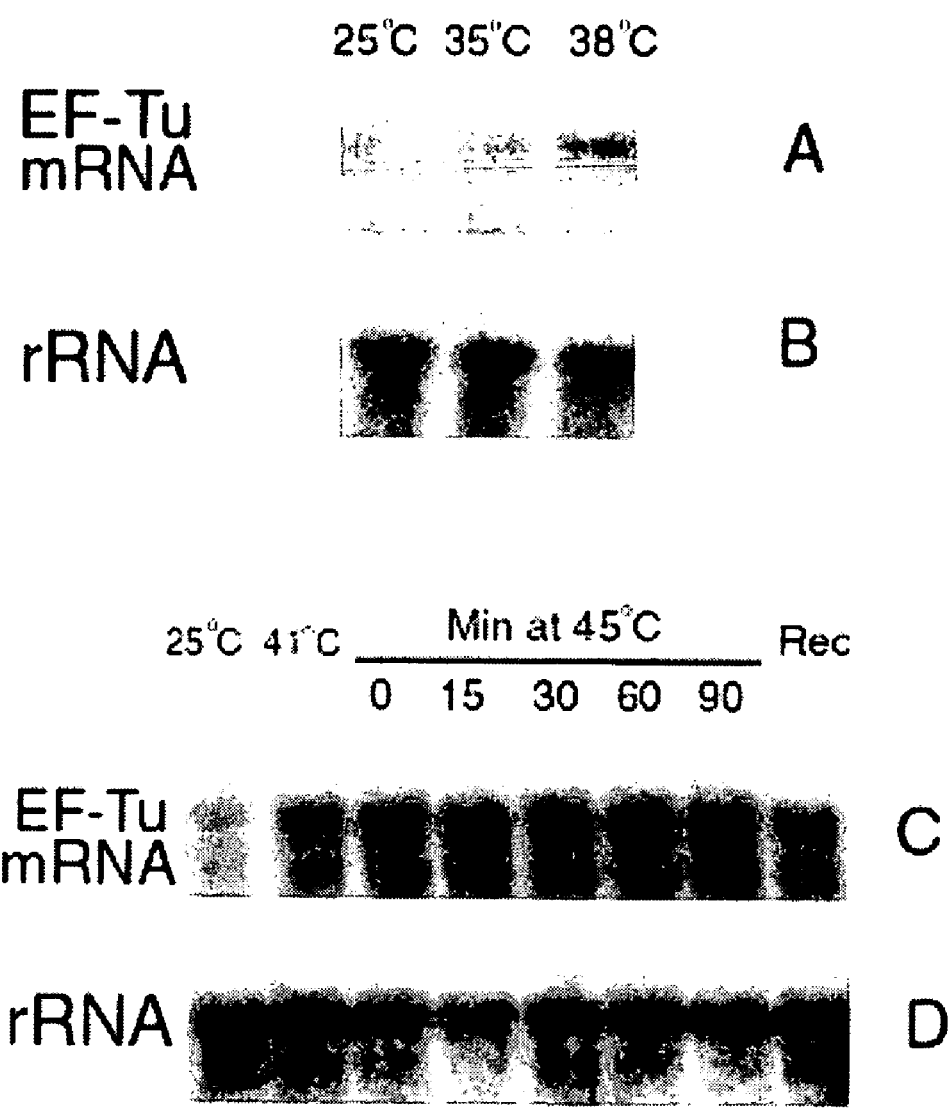
FIG. 4 is a Northern blot analysis of total RNA from the control and heat stressed plants of the ZPBL 1304 maize line. Leaf tissue (1.0 g) collected from the control and heat stressed plants was ground in liquid nitrogen and total RNA was extracted using RNAgents®, (Promega Corporation, U.S.A.). RNA was separated in 1% agarose gels followed by transfer to a Nylon membrane. The blots were probed using [$^{32}$P]dCTP labeled DNA probes for EF-Tu and 18S ribosomal RNA. (A) Northern blots showing the steady-state levels of EF-Tu mRNA in control plants (grown at 25° C.), and heat-stressed plants (at 35° C. and 38° C.). (B) The same blot (as in A) re-probed with 18s ribosomal DNA used as a positive control. (C) Northern blots showing heat-stress induced increase in the steady-state levels of EF-Tu mRNA at 25° C. (control), 41° C., and at various time duration at 45° C. (o min, 15 min, 30 min, 60 min, and 90 min). Rec, RNA isolated from the leaves of heat-treated plants after 2 hours of recovery at 25° C. (D) The same blot (as in C) re-probed with 18s ribosomal DNA used as a positive control.

The results show increased levels of EF-Tu mRNA during early stages of heat stress. Compared to control, a significant increase in the intensity of the hybridization band was observed at 41° C. and 45° C. (FIG. 4). The results suggest that during heat stress the synthesis of chloroplast protein synthesis elongation factor EF-Tu in ZPBL 1304 may be regulated at the level of transcription.

EXAMPLE 3

Identification of EF-Tu in the ZPBL 1304 Maize Line

Materials and Methods

Plant Material and Growth Conditions

Seeds of ZPBL 1304 (*Zea mays* L.) were washed with autoclaved distilled water and germinated in the dark on a single layer of moist germination paper. After three days, the seedlings were planted in pots (4 seedlings per pot) containing a mixture of soil: peat: sand (3:1:1, v/v/v). Plants were maintained in a growth chamber at 25/20° C. day/night temperature, 12 h photoperiod with 280 µumol $m^{-2}$ $s^{-1}$ light, 70% humidity and regular watering (Bhadula et al., 1998).

Isolation, Purification, and Sequencing of 45 HSPs

Three-week old plants were used for the isolation and purification of the 45 kD polypeptides. Plants were exposed to 45° C. heat stress for 3 h (Bhadula et al., 1998). Two hours after the beginning heat stress, the second leaf blades were labeled with 10 µL of [$^{35}$S]methionine (370 MBq/mL; specific activity 37 TBq/mmol, Amersham, Canada) for 1 h (Ristic et al., 1991). Control plants, maintained at 25° C., were simultaneously labeled. Following labeling, the leaves were harvested and used for protein extraction as described by Bhadula et al. (1998).

For sequencing, proteins were separated using 2-dimensional gel electrophoresis following the method of O'Farrell (1975) with some modifications (Bhadula et al., 1998). Isoelectric focusing (IEF) was carried out at 9,000 volt hours in glass tubes using 2% (v/v) Resolytes, pH 4-8 (BDH), 4% (w/v) acrylamide and 9 M urea. Sodium thioglycolate (100 µM) and 50 µM glutathione were added to the gel mixture to avoid the accumulation of free radicals (Dunbar et al., 1998). The IEF gels were removed from the tubes, washed in SDS-sample buffer (Laemmli, 1975) and mounted on top of a 10% (w/v) acrylamide gel. The gel running conditions were the same as described earlier (Bhadula et al., 1998).

The proteins from the 2-dimensional gel were transferred onto PVDF membranes (BioRad Laboratories, Calif.) using CAPS transfer buffer (Dunbar et al., 1997) at 900 mA for 3.5 h. The membranes were stained with 0.1% (w/v) amido black solution [prepared in 40% (v/v) methanol and 1% (v/v) acetic acid]. The 45 kD polypeptides were identified and their position was further confirmed by exposing the membranes to Kodak X-OMAT AR film. The 45 HSPs were clearly visible on the film and were matched with the stained membranes to confirm their position. The individual 45 kD polypeptide spots were cut from the blots and subjected to protein sequencing using automatic Edman degradation in a Procise 494 protein sequencer (Applied Biosystems Instruments). Proteins were sequenced at two facilities (protein sequencing facility at the University of Nebraska, Lincoln, Nev., and Iowa State University, Ames, Iowa).

Sub-Cellular Fractionation

The leaves were labeled with [$^{35}$S]methionine as described above. After labeling, the leaves were harvested and washed with sterile distilled water. The leaf blades were cut into small pieces and homogenized in chloroplast grinding medium (Fish and Jagendorf, 1982). The homogenate was passed through eight layers of cheesecloth and centrifuged at 200 g for 3 min using a Sorvall HB4 rotor. The resulting supernatant was centrifuged at 1500 g for 5 min. The pellet was suspended in a small volume of "suspend medium" (Fish and Jagendorf, 1982) and marked as "chloroplast-enriched fraction". Phase contrast microscopy revealed that this fraction contained mostly chloroplasts and some starch grains. The supernatant was marked as "1500 g supernatant."

Intact chloroplasts were purified from the chloroplast-enriched fraction according to the method of Fish and Jagendorf (1982) and examined with the phase contrast microscope. The purified chloroplasts appeared to be intact (phase bright) and free of any contamination. A small volume of chloroplast preparations was used for protein extraction and analysis. The chloroplasts were lysed by osmotic shock using distilled water in the presence of a protease inhibitor (1 mM phenylmethylsulfony fluoride) and also, by ultrasonication.

The "1500 g supernatant" was further centrifuged at 6,000 g for 10 min. The pellet containing broken chloroplasts, other cellular membranes and contaminating particulate fraction did not show the presence of 45 HSPs in 1-dimensional gels and was discarded. The 6,000 g supernatant was then centrifuged at 25,000 g for 15 min and the resulting pellet was re-suspended in a small volume of sterile distilled water containing 1 mM protease inhibitor and marked as "mitochondrial pellet." The 12,500 RPM supernatant was used as the "soluble fraction". A small volume of each fraction (chloroplast enriched fraction, purified chloroplasts, mitochondrial pellet and the soluble fraction) was used for protein quantification and trichloroacetic acid (TCA) counting according to the methods of Bradford (1976) and Mans and Novelli (1960), respectively. For electrophoresis, the remaining volume of the subcellular fractions was treated with SDS-sample buffer (1:1, v/v) (Laemmli, 1975), heated at 95° C. for 3 min, quickly cooled, and stored at −80° C. until used.

The protein samples from sub-cellular fractions were analyzed using 1-dimensional SDS-PAGE and autoradiography (Bhadula et al., 1998). Because we observed the 45 HSPs in the chloroplast and soluble fractions, these fractions were also analyzed using 2-dimensional gel electrophoresis and autoradiography (Bhadula et al., 1998). For comparison of protein synthesis patterns of subcellular fractions with total leaf proteins, [$^{35}$S]-labeled 'control' and 'heat-shocked' leaves were homogenized in SDS-sample buffer and the protein extracts were analyzed using 1-dimensional gel electrophoresis as described above.

Protein Synthesis by Isolated Chloroplasts

Chloroplasts were isolated as described above except that the leaves were not labeled with [$^{35}$S]methionine and no heat shock treatment was given to the plants. Chloroplasts were isolated and purified under sterile conditions. The purified chloroplasts were suspended in suspend buffer and divided into two lots ("control" and "heat shock"). The "control" lot was incubated in a protein synthesis mixture at 25° C. whereas the "heat shock" lot was incubated at 45° C. for 45 min. The incubation mixture contained 40 µL of the chloroplast preparation, 100 µL of suspend buffer, 5 µL of [$^{35}$S]-methionine and ATP (1 mM). Three inhibitors of protein synthesis, namely, cycloheximide (inhibitor of cytosolic protein synthesis), chloramphenicol (inhibitor of chloroplast and mitochondrial protein synthesis) and streptomycin (inhibitor of chloroplast protein synthesis) were also used separately (100 µM each), to find out if there was any contamination and subsequent protein synthesis by total cellular or mitochondrial fractions. The chloroplasts were illuminated at 1000 µMol m$^{-2}$s$^{-1}$. For each treatment, a proper control was incubated either in the dark or in the absence of ATP and inhibitors. After incubation, the chloroplasts were collected by centrifugation at 1500 g and washed twice with cold suspend buffer. The chloroplasts were then collected by centrifugation, lysed by osmotic shock and used for protein extraction, protein quantification, TCA counting and electrophoresis as described above.

Results

N-Terminal Sequence of 45 HSPs

Five polypeptides of the 45 HSP family were isolated for protein sequencing, and four of them [polypeptides 2, 3, 4, and 5 (Ristic et al., 1998a)] yielded reproducible amino acid sequences (Table 2). Polypeptides 2, 4 and 5 (Ristic et al., 1998a) had sequences similar to protein elongation factor EF-Tu of prokaryotes, lower eukaryotes, and chloroplast EF-Tu of higher plants. The sequence homology of the polypeptide 2 (from amino acids 4 to 20) varied from 88 to 820 with the EF-Tu of *Chlamydomonas reinhardtii* and *E. coli*, respectively (Jones et al., 1980; Baldauf and Palmer, 1990). The overall sequence of this polypeptide (20 amino acid stretch) showed 80% similarity with the chloroplast EF-Tu of several higher plants including *Arabidopsis thaliana* (Baldauf and Palmer, 1990). The polypeptides 4 and 5 were similar, and they showed 80 to 90% homology with EF-Tu from various prokaryotes, lower eukaryotes and chloroplast EF-Tu of higher plants (Jones et al., 1980; Baldauf and Palmer, 1990). N-terminal as well as internal sequence analysis of polypeptide 3 showed more than 80% homology with chloroplast glyceraldehyde 3-phosphate dehydrogenase (GAPDH) from various lower organisms and higher plants including *Zea mays* (Gowri and Campbell, 1989) and *Arabidopsis thaliana* (Shih et al., 1991). This polypeptide also exhibited high homology (75%) with GAPDH precursor from *Chlamydomonas reinhardtii* (Kersanach et al., 1994).

Subcellular Localization of 45 HSPs

The pattern of HSP synthesis in total leaf extracts and sub-cellular fractions is shown in FIGS. 1A and 1B, respectively. Control leaves did not synthesize the 45 kD proteins (FIG. 1A, lane 1). Heat-shock induced the synthesis of several high molecular mass (HMM, molecular mass >60 kD) and low molecular mass (LMM, molecular mass (<30 kD) and the 45 HSPs (FIG. 1A, lane 2). The pattern of protein synthesis in various subcellular fractions of control leaf extracts is not included since the 45 HSPs were not detected in the control leaves (FIG. 1A, lane 1).

The chloroplast fraction of the heat stressed leaves contained the majority of the 45 HSPs (FIG. 2B, lanes 3 and 4, indicated by arrows), with the purified chloroplast fraction enriched in these proteins (FIG. 1B, lane 3). Some LMM HSPs were also prominent in the purified chloroplast fraction (FIG. 1B, lane 3). Small amounts of the 45 HSPs were also detected in the cytosolic fraction (FIG. 1B, lane 1). The mitochondrial fraction, on the other hand, did not appear to contain proteins of 45 kD (FIG. 1B, lane 2). Instead, this fraction was enriched in some HMM and LMM HSPs (FIG. 1B, lane 2).

Two-dimensional gel analysis of purified chloroplast proteins revealed that several HSPs (LMM and HMM) including 45 HSPs were present in this fraction (FIG. 2A). Of the five 45 kD polypeptides (Ristic et al., 1998), three (polypeptides 1, 2, and 3) were localized in the chloroplasts and the polypeptide 2 [major 45 kD polypeptide (Ristic et al., 1998a)] appeared to be the most abundant (FIG. 2A, thick arrow). In addition, polypeptide 5, which was more prominent in the cytosolic fraction (FIG. 2B, thick arrow) was also detected in chloroplasts (FIG. 2A). Cytosolic fraction also contained polypeptide 4, which was not observed in the chloroplasts. Polypeptides 1, 2 and 3 were hardly detectable in the cytosolic fraction. Chloroplasts isolated from the leaves of control plants did not show the accumulation of proteins of 45 kD (FIG. 2C).

Protein Synthesis by Isolated Chloroplasts

Figure 2:
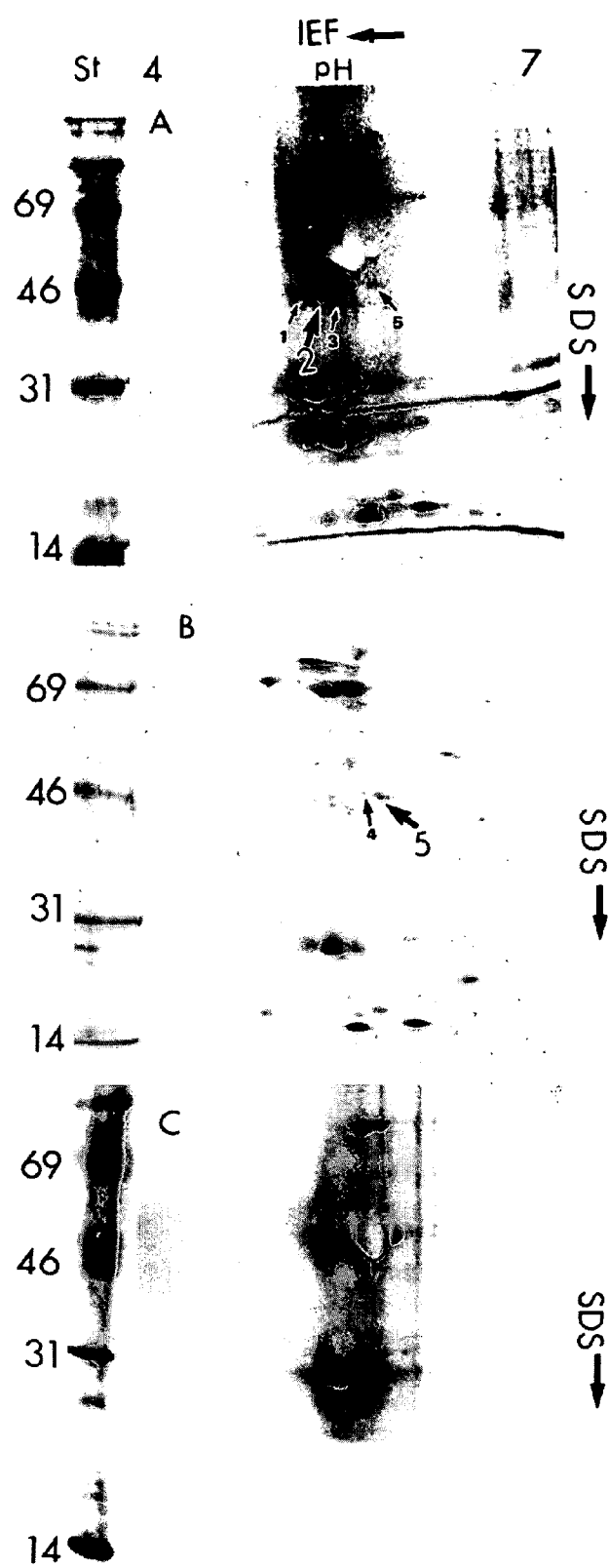
FIG. 2 is an autoradiograph of chloroplast proteins (A) and cytosolic proteins (B) from heat-shocked plants (analyzed by 2-dimensional gel electrophoresis of [$^{35}$S]-labeled proteins). The 45 kD HSPs (EF-Tu) are indicated by arrows (numbered 1-5) and the dominant proteins are marked with thick arrows. The 45 kD HSPs were not observed in control chloroplasts (C). Approximate molecular mass markers (in kilodaltons) are shown on the left side of the autoradiograph.
Figure 3:
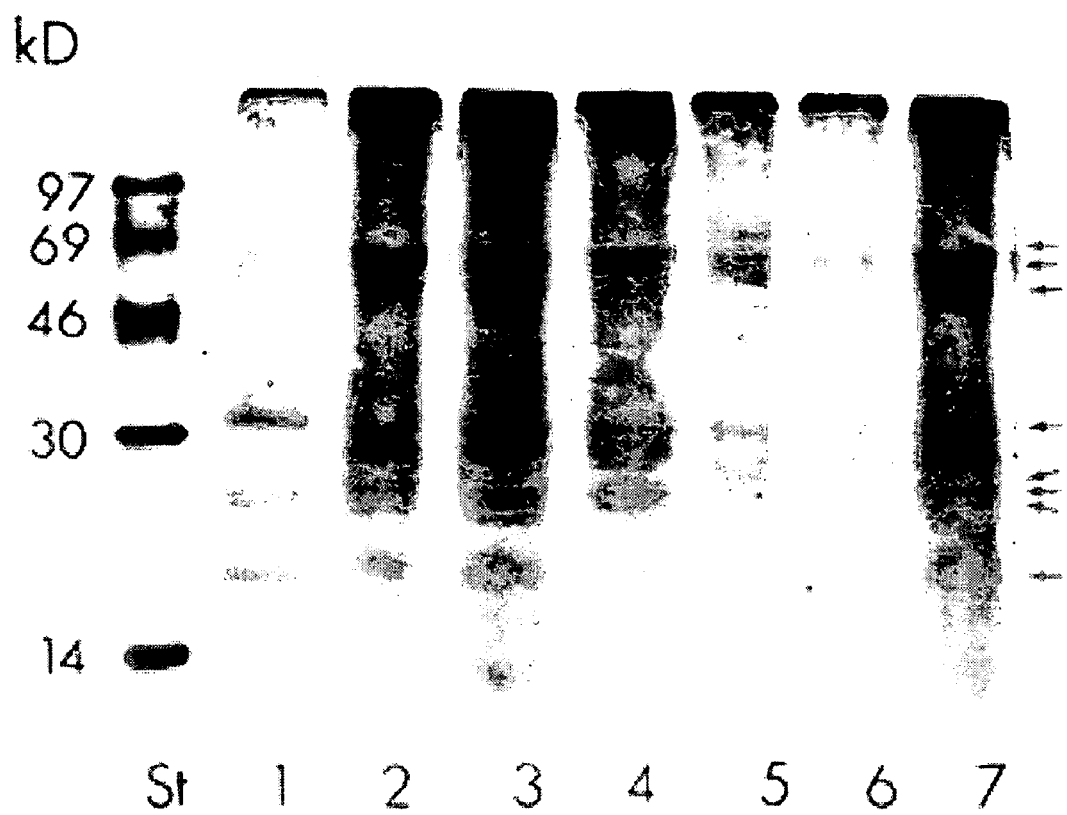
FIG. 3 is an autoradiograph showing protein synthesis by isolated chloroplasts of ZPBL 1304 at 45° C. (lane 1-6) and 25° C. (lane 7). Lane 1, protein synthesis in the dark in presence 1 mM ATP; lane 2, light (1000 µmol m$^{-2}$s$^{-1}$); lane 3, light+1 mM ATP; lane 4, light+100 µM cycloheximide; lane 5, light+100 µM Streptomycin; lane 6, light+100 µ Chloramphenicol; lane 7, light+ATP at 25° C. Arrows indicate proteins synthesized by isolated chloroplasts. St, standard molecular markers. Note that the 45 kD HSPs were not synthesized by isolated chloroplasts. Approximate molecular mass markers (in kilodaltons) are shown on the left side of the autoradiograph.

The pattern of protein synthesis in isolated control (incubated at 25° C.) and heat-shocked (incubated at 45° C.) chloroplasts is shown in FIG. 3 (lanes 1-6: heat shocked chloroplasts; lane 7: control chloroplasts). In both heat-shocked and control chloroplasts, no incorporation of the label into proteins was observed in the dark (not shown). However, protein synthesis in the chloroplasts incubated in the dark was initiated by the addition of ATP, and within 15 min of incubation, the synthesis of several polypeptides was observed (FIG. 3, lane 1) indicating that the process of protein synthesis in isolated chloroplasts was energy-dependent. Illumination of chloroplasts (1000 PuMol m$^{-2}$ s$^{-1}$) at 45° C. resulted in the synthesis of several polypeptides (FIG. 2, lane 2). Addition of ATP to the illuminated chloroplasts did not cause a significant increase in the accumulation of proteins (FIG. 3, lane 3) suggesting that isolated chloroplasts were able to generate sufficient ATP. As a general rule, protein synthesis in isolated chloroplasts was sensitive to both, chloramphenicol and streptomycin, but not to cycloheximide (FIG. 3, lanes 4-6). This further confirms the purity of chloroplasts used in this study. The pattern of protein synthesis in the chloroplasts incubated at 25° C. (FIG. 3, lane 7) was similar to that observed for chloroplasts incubated at 45° C. (FIG. 3, lane 2) indicating that isolated chloroplasts did not synthesize any HSPs including the 45 HSPs.

Discussion

Identification of proteins using N-terminal sequencing and determination of their subcellular origin and distribution is a primary step towards developing an understanding of their physiological function. In this study, the identity, subcellular localization, and origin of the 45 kD heat-shock polypeptides (polypeptides 1-5, Ristic et al., 1998) from the drought and heat tolerant maize line ZPBL 1304 were investigated. N-terminal sequence analysis revealed that the major 45 kD polypeptide 2, and polypeptides 4 and 5 had amino acid sequences similar to chloroplast protein elongation factor EF-Tu, and polypeptide 3 matched the sequence of chloroplast GAPDH. The study on sub-cellular localization showed that the polypeptides 1, 2, 3, and 5, were localized in the chloroplasts, although polypeptide 5 was also present in the cytosol. Polypeptide 4 was detected only in the cytosol. The study on protein origin revealed that chloroplast polypeptides of 45 kD were synthesized in the cytosol. The results on subcellular localization and origin of 45 kD polypeptides are, thus, consistent with the sequence data. Combined, they suggest that major fraction of 45 kD proteins is chloroplast protein synthesis elongation factor (EF-Tu) and a minor fraction is chloroplast GAPDH.

The study has revealed the synthesis of three heat-induced polypeptides with high sequence homology to the chloroplast elongation factor, EF-Tu. The molecular mass of the polypeptides identified as EF-Tu (45 kD) is similar to the molecular mass of EF-Tu from higher plants and other organisms (Jacobson and Rosenbusch, 1976; Young and Bernlohr, 1991; Berchtold et al., 1993; Ursin et al., 1993). The appearance of three polypeptides of 45 kD with high sequence homology to the chloroplast EF-Tu indicates that there may be a polymorphism in the EF-Tu genes which may be related to spatial and/or temporal regulation of the cell metabolism under heat stress. Ursin et al., (1993) have reported two copies of EF-Tu gene in tobacco.

Whereas the major 45 kD polypeptide (polypeptide 2) showing EF-Tu sequence was clearly chloroplastic, two other EF-Tu polypeptides (polypeptides 4 and 5) were detected in the cytosol. The presence of 45 kD polypeptides in the cytosol is not surprising since chloroplast EF-Tu is known to be encoded by nuclear genes and synthesized in the cytosol (Baldauf and Palmer, 1990). Furthermore, nuclear-encoded chloroplast proteins can also be found in the cytosol. For example, Heckathon et al. (1998) reported the accumulation of nuclear-encoded chloroplast proteins in the cytosol during severe heat stress. The presence of EF-Tu polypeptides 4 and 5 in the cytosolic fractions may also suggest a possible role of these polypeptides in the cytosol or in the organelles other than chloroplasts and mitochondria. EF-Tu has been shown to be associated with plasma membrane in *E. coli* where it plays a structural role (Jacobson and Rosenbusch, 1976).

EF-Tu is a highly conserved protein and plays a role in polypeptide elongation during protein synthesis (Riis et al., 1990). It is a GTP binding protein (Young and Bernlohr, 1991) and functions in the binding and transport of codon-specific tRNA at the aminoacyl site on the ribosome (Brot, 1977). EF-Tu has been shown to have other functions in addition to its role in polypeptide elongation (Travers et al., 1970; Jacobson and Rosenbusch, 1976; Young and Bernlohr, 1991). One of these functions is implicated in thermotolerance. Kudlicki et al. (1997) reported a chaperone-like property of bacterial EF-Tu in the refolding of denatured rhodanese. Similarly, Caldas et al. (1998) described the chaperone properties of prokaryotic EF-Tu and found that like other molecular chaperones, *E. coli* EF-Tu interacts with unfolded and denatured proteins and forms stable complexes. Prokaryotic EF-Tu was also found to protect citrate synthase and α-glucosidase from thermal aggregation, and the chaperone properties of EF-Tu were shown to occur at very low levels (20-fold lower than cellular concentrations) (Caldas et al., 1998). Prokaryotic and eukaryotic EF-Tu are strikingly similar (Riis et al., 1990), and it is possible that maize EF-Tu may have chaperone activity similar to prokaryotic EF-Tu.

Since heat stress is known to cause significant damage to chloroplast membranes, it is possible that increased synthesis of chloroplast EF-Tu in the ZPBL maize line may be related to the stability of chloroplast membranes at high temperatures and may also stabilize chloroplast protein synthesis. Indeed, chloroplasts from the heat tolerant line of maize (ZPBL 1304), that synthesizes EF-Tu during heat stress have been found to be more heat stable than the chloroplasts from the line that does not synthesize EF-Tu (heat sensitive line, ZPL 389) (Ristic and Cass, 1992, 1993). Furthermore, under heat shock conditions, isolated chloroplasts of the heat tolerant line (ZPBL 1304) were able to synthesize all the proteins that were observed in control chloroplasts (FIG. 3).

The involvement of EF-Tu with thermotolerance in eukaryotes including higher plants has not been reported. The results of our study show that in the ZPBL 1304 maize line, EF-Tu is induced during heat-shock.

TABLE 2

Amino acid sequences of four polypeptides of the 45 kD HSP family. 'X' indicates unidentified amino acid. Homology of these sequences with proteins from various organisms is described in the text. GAPDH: Glyceraldehyde 3-phosphate dehydrogenase. The sequence in parenthesis shows internal sequence of the GAPDH polypeptide.

| NO.* | Sequence | SEQ ID NUMBERS | Homology |
|---|---|---|---|
| 2 | AXNKFERLKPHVNTGXIGHV | (SEQ ID NO:1) | Protein elongation factor (EF-Tu) |
| 3 | AVKVTINGFGRIGTNFLTEA | (SEQ ID NO:2) | GAPDH |
|   | (VVAWYDNEXGYS) | (SEQ ID NO:3) |   |
| 4 | ARGKFERTKPHVNIGTIXHV | (SEQ ID NO:4) | Protein elongation factor (EF-Tu) |
| 5 | RGKFERTKPHVNIGTIXXV | (SEQ ID NO:5) | Protein elongation factor (EF-Tu) |

*Polypeptide No. (Ristic et al., 1999)

EXAMPLE 4

Identification of Maize EF-Tu ESTs

We obtained EF-Tu peptide sequence from protein spots showing differential abundance on 2-D gels. The inventors then used this sequence and blasted it against our maize EST database. Multiple ESTs had translated homology with the protein sequence. Upon blasting these ESTs against the public database, it was found that they matched various EF-Tu genes. We selected one clone (CHSTG79R) that had high homology (BLAST Score=333) with a tobacco chloroplast elongation factor. This EST came from a cDNA library that was constructed from B73 seedlings that were drought and heat stressed.

Details of cDNA Library

Seedlings from the inbred B73 were established in soil and droughted for 10-days. Seedlings were then heat shocked for 24 hrs and allowed to recover. The aerial plant material was harvested, frozen in liquid N, and RNA was extracted from this tissue and used to create the cDNA library (P0018).

Sequencing of CHSTG79R

The CHSTG79R clone appeared to be full length (~1.4 kb), and the DNA Core Facility sequenced the insert (SEQ ID NO:6, FIG. 7).

EXAMPLE 5

Expression of Maize Chloroplast Protein Synthesis Elongation Factor, EF-Tu, Enhances *Escherichia coli* Viability Under Heat Stress Materials and Methods Maize cDNA for EF-Tu was cloned into an *E. coli* expression vector, pTrcHis2 (promoter, TRC). *E. coli* transformats for maize EF-Tu were then grown at 37° C. and subsequently diluted with a fresh LB medium supplemented with ampicillin (100 μg mL$^{-1}$) and IPTG to a final concentration of 1 mM. Two hours after induction, cultures were diluted, and 1 mL samples were exposed to 55° C. for 1 h. Aliquots were taken at 0 and 1 h, and dilutions were plated in triplicate onto agar growth medium containing ampicillin. Plated cells were incubated overnight at 37° C., and cell viability was assessed by counting the number of colonies after incubation.

Results and Conclusion

Figure 5:
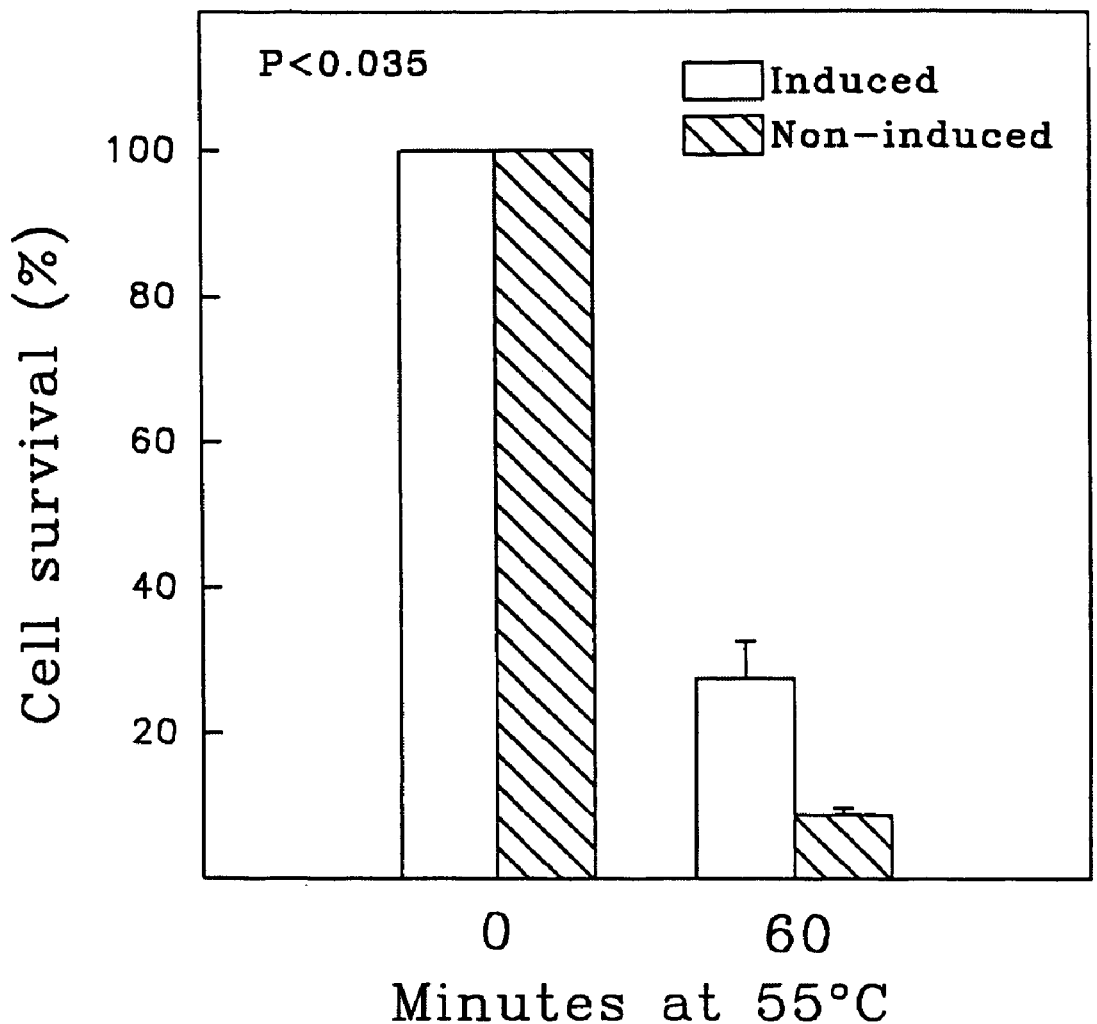
FIG. 5 is a depiction of the viability of *E. coli* transformants for maize EF-Tu subjected to 55° C. treatment. Culture samples were taken after 0 and 60 min of exposure to high temperature. Following high temperature treatment, samples were plated onto agarose growth medium and incubated overnight at 37° C. Colonies were counted, and cell viability (survival) was plotted as the percentage of colony-forming units relative to the starting number of colonies at time 0. Means of 4 independent experiments are shown. Bars indicate standard errors. Note that cells over-expressing maize EF-Tu (induced) show higher viability compared to cells not over-expressing EF-Tu (non-induced).

The results showed that *E. coli* over-expressing maize EF-Tu displayed increased viability after exposure to heat stress (FIG. 5). The number of *E. coli* colonies, that grew at 37° V following heat stress, was 18% higher (P<0.038) in induced cells (cells producing maize EF-Tu) than in non-induced cells (cells not producing maize EF-Tu). The results strongly suggest that maize EF-Tu plays an important role in protection against heat injury.

EXAMPLE 6

Relationship Between the Levels of EF-Tu and Heat Tolerance in "Pioneer" Maize Hybrids We investigated the correlation between the levels of EF-Tu and the plant ability to withstand heat stress. Three more heat tolerant and four less heat tolerant maize hybrids were used (Ristic et al., 1998). Two-week growth-chamber grown plants were exposed to 45° C. for 24 h followed by 5-d recovery. For EF-Tu analysis, leaf samples were collected after 3 h of exposure to heat stress. Proteins were extracted and analyzed using western blotting. The relative amount of EF-Tu was estimated by determining band volume, using Molecular Analyst (BioRad) (Bhadula et al., Heat-stress induced synthesis of chloroplast protein synthesis elongation factor (EF-Tu) in a heat-tolerant maize line, *Planta* (2001) 212:359-366. Plant heat tolerance was assessed by examining damage to the thylakoid membranes estimated using chlorophyll a fluorescence after 5-d recovery (Ristic et al. 1998).

Figure 6A:
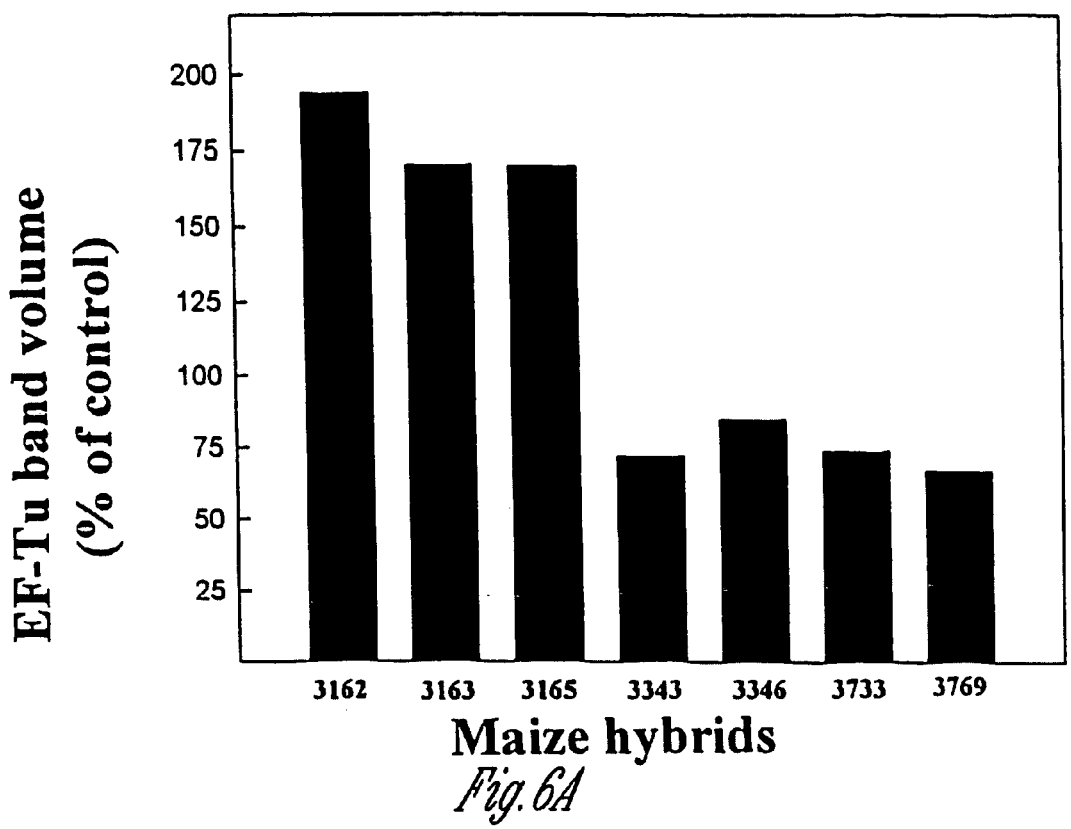
FIG. 6 is a depiction of the heat-induced accumulation of maize EF-Tu (A and D), and damage to the thylakoid (B) membranes in maize hybrids with contrasting heat tolerance. Damage to thylakoid membranes was estimated by measuring chlorophyll α fluorescence and calculating the ratio of constant fluorescence (O) and the peak of variable fluorescence (P). The increase in O/P ratio indicates damage to thylakoid membranes (Ristic et al., 1998). Bars indicate standard errors (n=5). D, Western blot showing heat-induced accumulation of EF-Tu (C, control plants; HS, heat-stressed plants). EF-Tu bands (indicated by arrows) were scanned and the band volume of heat-stressed plants was calculated as W of control and plotted in "A".
Figure 6B:
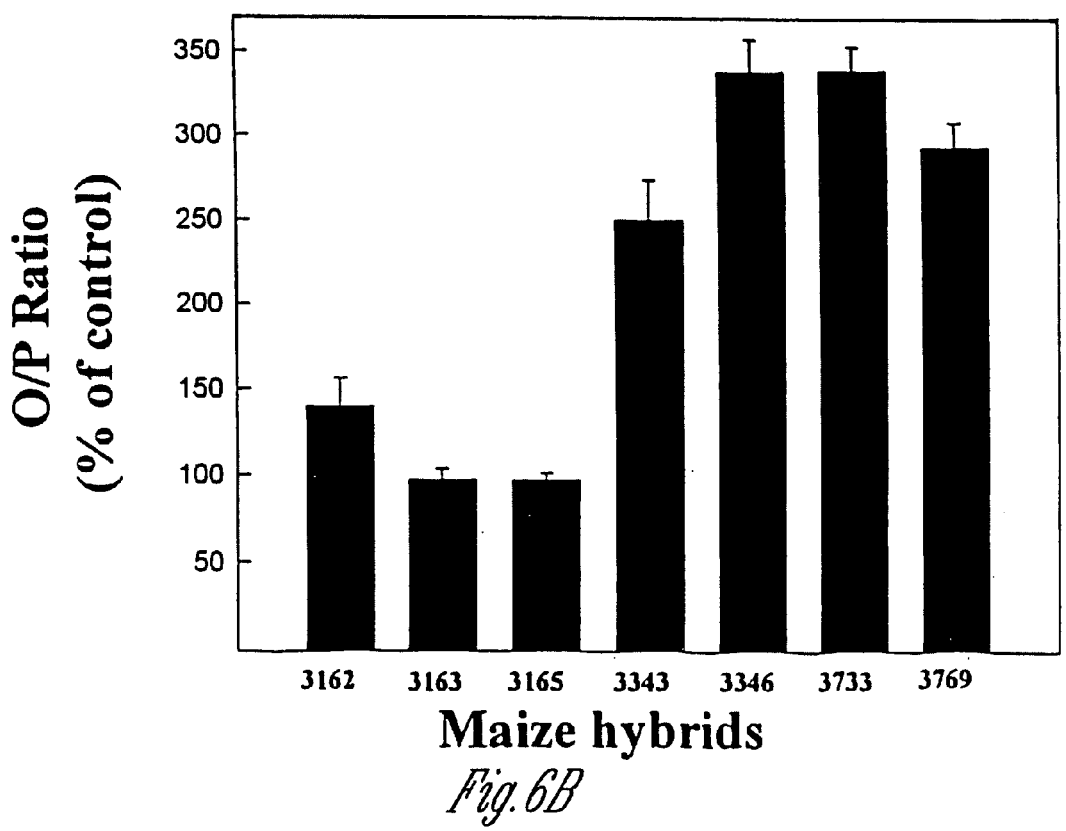
Figure 6C:
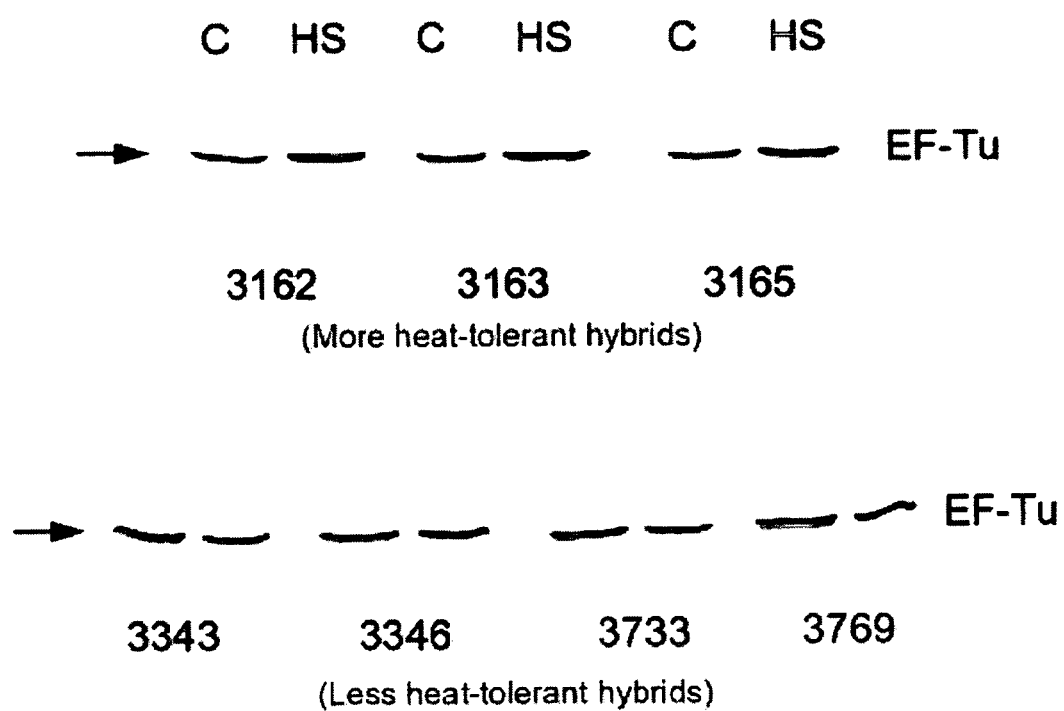

Western blots revealed that the hybrids that better withstand heat stress also show higher accumulation of the EF-Tu under heat stress conditions (FIG. 6). More heat tolerant hybrids (hybrids 3162, 3163, 3165) had higher EF-Tu band volume (FIGS. 6A and D) and lower damage to the thylakoid membranes (FIG. 6B) than less heat tolerant hybrids (hybrids 3343, 3346, 3733, 3739). The results strongly support the hypothesis that maize EF-Tu plays a role in the development of heat tolerance.

All articles cited herein and in the following list are hereby expressly incorporated in their entirety by reference.

CITATIONS

Bauldauf et al. (1990) Evolutionary transfer of the chloroplast tufA gene to the nucleus. Nature 344:262-265.

Bhadula et al. (1998) Synthesis of a family of 45 ku heat shock proteins in a drought and heat resistant line of maize under controlled and field conditions. J. Plant Physiol 152:104-111.

Bhadula et al. (1999) Plant Biology 99:559.

Bhadula et al. (2000a) Heat-stress induced synthesis of chloroplast protein synthesis elongation factor (EF-Tu) in a heat-tolerant maize line. Planta (in press).

Berchtold et al. (1993) Crystal structure of active elongation factor Tu reveals major domain rearrangements. Nature 365:126-132.

Bradford, M. M. (1976) A rapid and sensitive method for quantitation of microgram quantities of protein utilizing the principle of protein-dye binding. Anal Biochem 72:248-254.

Brot, N. (1977) Translation. In H. Weissbach and S. Pestka, eds, Molecular Mechanisms of Protein Synthesis, Academic Press, New York, pp. 374-411.

Caldas et al. (1998) Chaperone properties of bacterial elongation factor. J Biol Chem 273:11478-11482.

Dunbar et al. (1997) Identification of plant mitochondrial proteins: a procedure linking two-dimensional gel electrophoresis of protein sequencing from PVDF membranes using a fastblot cycle. Plant Mol Biol Rep 15:46-61.

Fish et al. (1982) High rates of protein synthesis by isolated chloroplasts. Plant Physiol 70:1107-1114.

Gowri et al. (1989) cDNA clones for corn leaf NADH:nitrate reductase and chloroplast NAD(P)+: glyceraldehyde-3-phosphate dehydrogenase. Plant Physiol 90:792-798.

Heckathorn et al. (1998) Nuclear-encoded chloroplast proteins accumulate in the cytosol during severe heat stress. International J Plant Sci 159:39-45.

Jacobson et al. (1976) Abundance and membrane association of elongation factor Tu in *E. coli*. Nature 261:23-26.

Jones et al. (1980) The complete amino-acid sequence of elongation factor Tu in *Escherichia coli*. Eur J Biochem 108:507-526.

Kersenach et al. (1994) Five identical intron positions in ancient duplicated genes of eubacterial origin. Nature 367:387-389.

Kudlicki et al. (1997) Renaturation of rhodanses by translational elongation factor (EF) Tu:Protein refolding by EF-Tu flexing. J Biol Chem 272:32206-32210.

Laemmli, U. K. (1970) Cleavage of structural proteins during the assembly of the head of bacteriophase T4. Nature 227:680-685.

Lindquist, S. (1986) The heat shock response. Ann Rev Biochem. 55:1151-1191.

Mans et al. (1960) A convenient, rapid and sensitive method for measuring the incorporation of radioactive amino acids into protein. Biochem Biophys Res Comm 3:540-543.

O'Farrell, P. H. (1975) High resolution two-dimensional electrophoresis of protein. J Biol Chem 250:4007-4021.

Riis et al. (1990) Eukaryotic protein elongation factors. TIBS 15:420-424.

Ristic et al. (1991) Heat shock proteins in two lines of *Zea mays* L. that differ in drought and heat resistance. Plant Physiol 97, 1430-1434.

Ristic et al. (1992) Chloroplast structure after water and high-temperature stress in two lines of maize that differ in endogenous levels of abscisic acid. International J. Plant Sci. 153:186-196.

Ristic et al. (1993) Dehydration avoidance and damage to the plasma and thylakoid membranes in lines of maize differing in endogenous levels of abscisic acid. J. Plant Physiol. 142:759-764.

Ristic et al. (1996) Dehydration, damage to cellular membranes and heat-shock proteins in maize hybrids from different climates. J. Plant Physiol 149:424-432.

Ristic et al. (1998a) Two-dimensional gel analysis of 45 ku heat shock proteins from a drought and heat resistant maize line. J. Plant Physiol. 154:264-268.

Ristic et al. (1998b) Evidence of association between specific heat-shock protein(s) and the drought and heat tolerance phenotype in maize. J. Plant Physiol 153:497-505.

Travers et al. (1970) Factor necessary for ribosomal RNA synthesis. Nature 228:748-751.

Ursin et al. (1993) Cloning and nucleotide sequence of tobacco chloroplast translational elongation factor, EF-Tu. Plant Physiol 101:333-334.

Vierling, E. (1991) The roles of heat shock proteins in plants. Ann Rev Plant Physiol Plant Mol Biol 42:579-620.

Waters et al. (1996) Evolution, structure and function of the small heat shock proteins in plants. J Expt Bot 47:325-338.

Young et al. (1991) Elongation factor Tu is methylated in response to nutrient deprivation in *Escherichia coli*. J Bacteriol 173:3096-3100.

What is claimed is:

1. A purified and isolated nucleotide sequence having at least 90% identity to the full length of SEQ ID NO: 6 and which encodes upon expression an EF-Tu protein characterized by the following:
   (a) is approximately 45 kD;
   (b) is expressed natively under heat shock conditions;
   (c) wherein when the protein is expressed natively under heat shock conditions, said protein is synthesized in the cytoplasm and localized in chloroplasts; and
   (d) wherein expression of said protein increases heat tolerance or heat and drought tolerance in plants.

2. An expression construct comprising: a nucleotide sequence according to claim 1, operatively linked to a regulatory region that directs expression in a plant cell, wherein said protein is localized in chloroplasts when the construct is present in a plant cell.

3. A vector capable of transforming or transfecting a host cell, said vector comprising an expression construct according to claim 2.

4. The vector of claim 3 wherein said vector is a plasmid based vector.

5. The vector of claim 3 wherein said vector is a viral based vector.

6. A bacterial or plant host cell transformed or transfected with a vector according to claim 3.

7. The host cell of claim 6 wherein said cell is a plant cell.

8. A method for increasing plant tolerance to heat or heat and drought comprising: transforming a plant cell with a genetic construct comprising: a nucleotide sequence having at least 90% identity to the full length of SEQ ID NO: 6 and which encodes an Ef-Tu protein characterized by the following:
   (a) is approximately 45 kD;
   (b) is expressed natively under heat shock conditions; and
   (c) wherein when the protein is expressed natively under heat shock conditions, said protein is synthesized in the cytoplasm and localized in chloroplasts; and
   (d) wherein expression of said protein increases heat tolerance or heat and drought tolerance in plants;
   said nucleotide sequence being operably linked to promoter or regulatory regions capable of inducing expression in a transgenic plant or transgenic plant tissue; and regenerating a transgenic plant from said transformed cell, wherein the Ef-Tu protein encoded by said nucleotide sequence is localized in chloroplasts in the transgenic plant, wherein said transgenic plant exhibits increased heat tolerance or heat and drought tolerance.

9. The method of claim 8 wherein at least one of said promoter or regulatory regions causes expression during stress.

10. The method of claim 8 wherein said promoter is selected from the group consisting of: a constitutive, an inducible, and an organ specific promoter.

11. The method of claim 8 wherein said expression construct further comprises a selectable marker gene.

12. A transgenic plant containing a DNA construct comprising a polynucleotide having at least 90% identity to the full length of SEQ ID NO: 6 and encoding EF-Tu protein operably linked to a promoter, wherein the EF-Tu protein is localized in chloroplasts so that the transgenic plant exhibits increased tolerance to one or more conditions selected from the group consisting of excess heat and drought, wherein said increased tolerance is not present in a corresponding plant not containing the DNA construct, wherein said Ef-Tu protein is characterized by the following:
   (a) is approximately 45 kD:
   (b) is synthesized natively under heat shock conditions in cytoplasm and localizes to chloroplasts.

13. A seed produced by the transgenic plant of claim 12 wherein said seed comprises the DNA construct.

14. A progeny transgenic plant derived from the transgenic plant of claim 12 wherein said progeny plant expresses said DNA construct so that the progeny plant exhibits said increased tolerance.

15. A transgenic plant according to claim 12 wherein the plant is a maize plant.

16. A seed derived from the progeny plant of claim 14 wherein said seed comprises the DNA construct.

17. A transgenic plant according to claim 12 wherein the plant is obtained by a process comprising the steps of:
  bombarding intact regenerable plant cells with microprojectiles coated with the DNA construct;
  identifying or selecting a population of transformed cells; and
  regenerating a transgenic plant therefrom.

18. A method according to claim 8 further including the step of obtaining progeny from the transformed plant wherein said progeny comprise said construct.

19. A method according to claim 18 wherein the progeny are obtained by crossing the transformed plant with an inbred line.

20. A method according to claim 18 further including the step of:
  obtaining seed from the progeny and obtaining further progeny plants comprising the construct from the seed.

* * * * *